US008293880B2

(12) United States Patent
Cote et al.

(10) Patent No.: US 8,293,880 B2
(45) Date of Patent: Oct. 23, 2012

(54) PROGNOSTIC PANEL FOR URINARY BLADDER CANCER

(75) Inventors: Richard J. Cote, Miami, FL (US); Anirban P. Mitra, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 519 days.

(21) Appl. No.: 12/411,199

(22) Filed: Mar. 25, 2009

(65) Prior Publication Data

US 2009/0246790 A1 Oct. 1, 2009

Related U.S. Application Data

(60) Provisional application No. 61/039,351, filed on Mar. 25, 2008.

(51) Int. Cl.
C07H 21/04 (2006.01)
C12Q 1/68 (2006.01)
(52) U.S. Cl. .................. 536/23.1; 536/24.3; 435/6.1
(58) Field of Classification Search .................. None
See application file for complete search history.

(56) References Cited

U.S. PATENT DOCUMENTS

2009/0215053 A1* 8/2009 Galon et al. .................. 435/6

OTHER PUBLICATIONS

Mitra, A.P. et al., Molecular staging of bladder cancer, BJU International 96:7-12, 2005.
Brambilla, C. et al., Early detection of lung cancer: role of biomarkers., Eur Respir J Suppl 39:36s-44s, 2003.
Northup, J.K. et al., Do cytogenetic abnormalities precede morphologic abnormalities in a developing malignant condition?, Eur J Haematol 78:152-6, 2007.
Mitra, A.P. et al., Molecular pathways in invasive bladder cancer: New insights into mechanisms, progression, and target identification, J Clin Oncol 24:5552-64, 2006.
Willey, J.C. et al., Expression measurement of many genes simultaneously by quantitative RT-PCR using standardized mixtures of competitive templates, Am J Respir Cell Mol Biol 19:6-17, 1998.
Pagliarulo, V. et al., Sensitivity and reproducibility of standardized-competitive RT-PCR for transcript quantification and its comparison with real time RT-PCR, Mol Cancer 3:5, 2004.
Mitra, A.P. et al., The use of genetic programming in the analysis of quantitative gene expression profiles for identification of nodal status in bladder cancer, BMC Cancer 6:159, 2006.
Miller, R.G., Survival analysis. Wiley series in probability and mathematical statistics, New York, N.Y., John Wiley, 1981, pp. 44-102.
Berry, G. et al., Mock PA: A comparison of two simple hazard ratio estimators based on the logrank test, Stat Med 10:749-55, 1991.
Harrell, F.E., Jr. et al., Multivariable prognostic models: Issues in developing models, evaluating assumptions and adequacy, and measuring and reducing errors, Stat Med 15:361-87, 1996.
Chen, C.H. et al., The bootstrap and identification of prognostic factors via Cox's proportional hazards regression model, Stat Med 4:39-46, 1985.
Altman, D.G. et al., Bootstrap investigation of the stability of a Cox regression model, Stat Med 8:771-83, 1989.
Therneau, T.M. et al., An introduction to recursive partitioning using the RPART routines, Mayo Clinic Biostatistics Technical Report, Rochester, MN, Mayo Foundation, 1997.
Akaike, H., A new look at the statistical model identification, IEEE Trans Automat Contr AC-19:716-23, 1974.
Dijkstra, E.W., A note on two problems in connexion with graphs, Numer Math 1:269-71, 1959.
Sanchez-Carbayo M. et al., Defining molecular profiles of poor outcome in patients with invasive bladder cancer using oligonucleotide microarrays, J Clin Oncol 24:778-89, 2006.
Braakhuis, B.J. et al., A genetic explanation of Slaughter's concept of field cancerization: Evidence and clinical implications, Cancer Res 63:1727-30, 2003.
Affymetrix: Array design for the GeneChip Human Genome U133 Set (Part No. 701133 Rev. 2). Santa Clara, CA, 2007.
Tiniakos, D.G. et al., c-jun oncogene expression in transitional cell carcinoma of the urinary bladder, Br J Urol 74:757-61, 1994.
Itoh, M. et al., Requirement of STAT3 activation for maximal collagenase-1 (MMP-1) induction by epidermal growth factor and malignant characteristics in T24 bladder cancer cells, Oncogene 25:1195-204, 2006.
Schultz, I.J. et al., Prediction of recurrence in Ta urothelial cell carcinoma by real-time quantitative PCR analysis: A microarray validation study, Int J Cancer 119:1915-9, 2006.
Kuo, W.P. et al., Analysis of matched mRNA measurements from two different microarray technologies, Bioinformatics 18:405-12, 2002.
Zhao, H. et al., Plasma levels of insulin-like growth factor-1 and binding protein-3, and their association with bladder cancer risk, J Urol 169:714-7, 2003.
Hussain, S.A. et al., BCL2 expression predicts survival in patients receiving synchronous chemoradiotherapy in advanced transitional cell carcinoma of the bladder, Oncol Rep 10:571-6, 2003.

(Continued)

Primary Examiner — Kenneth R. Horlick
Assistant Examiner — David Thomas
(74) Attorney, Agent, or Firm — Seth D. Levy; Nixon Peabody LLP

(57) ABSTRACT

The present invention relates to methods of prognosing urothelial carcinoma. In one embodiment, the present invention provides a method of prognosing urothelial carcinoma by determining expression levels of JUN, MAP2K6, STAT3 and/or ICAM1. In another embodiment, the present invention provides an single prognostic panel made up of eight gene markers. In another embodiment, the present invention provides a single prognostic panel made up of eleven gene markers.

14 Claims, 29 Drawing Sheets

OTHER PUBLICATIONS

Blaveri, E. et al., Bladder cancer outcome and subtype classification by gene expression, Clin Cancer Res 11:4044-55, 2005.

Korkolopoulou, P. et al., Differential expression of bcl-2 family proteins in bladder carcinomas. Relationship with apoptotic rate and survival, Eur Urol 41:274-83, 2002.

Nakakuki, K. et al., Novel targets for the 18p11.3 amplification frequently observed in esophageal squamous cell carcinomas, Carcinogenesis 23:19-24, 2002.

Kraemer, K. et al., Microarray analyses in bladder cancer cells: Inhibition of hTERT expression down-regulates EGFR, Int J Cancer 119:1276-84, 2006.

Gonzales, R. et al., Superoxide dismutase, catalase, and glutathione peroxidase in red blood cells from patients with malignant diseases, Cancer Res 44:4137-9, 1984.

Steele, L.P. et al., Differential susceptibility to Trail of normal versus malignant human urothelial cells, Cell Death Differ 13:1564-76, 2006.

Ren, R. et al., Gene expression profiles identify a role for cyclooxygenase 2-dependent prostanoid generation in BMP6-induced angiogenic responses, Blood 109:2847-53, 2007.

Schnakenberg, E. et al., Susceptibility genes: GSTM1 and GSTM3 as genetic risk factors in bladder cancer, Cytogenetics & Cell Genetics 91:234-8, 2000.

Chatterjee, S.J. et al., Combined effects of p53, p21, and pRb expression in the progression of bladder transitional cell carcinoma, J Clin Oncol 22:1007-13, 2004.

Shariat, S.F. et al., p53, p21, pRB, and p16 expression predict clinical outcome in cystectomy with bladder cancer. J Clin Oncol 22:1014-24, 2004.

\* cited by examiner

Figure 3A.

| | n | Recurrence | | | Overall Survival | | |
|---|---|---|---|---|---|---|---|
| | | Relative Risk of Recurring (95% CI)* | Probability ± SE† of 5-year recurrence | P value* | Relative Risk of Dying (95% CI)* | Probability ± SE† of 5-year survival | P value* |
| Study cohort | 58 | | 0.56 ± 0.08 | | | 0.38 ± 0.07 | |
| Age | | | | 0.48 | | | 0.49 |
| ≤69 years | 28 | 1.00 (Reference) | 0.47 ± 0.10 | | 1.00 (Reference) | 0.43 ± 0.10 | |
| ≥70 years | 30 | 1.30 (0.62, 2.70) | 0.63 ± 0.10 | | 1.24 (0.64, 2.40) | 0.34 ± 0.09 | |
| Sex | | | | 0.28 | | | 0.28 |
| Male | 49 | 1.00 (Reference) | 0.51 ± 0.08 | | 1.00 (Reference) | 0.39 ± 0.07 | |
| Female | 9 | 1.63 (0.66, 4.01) | 0.80 ± 0.17 | | 1.56 (0.68, 3.59) | 0.33 ± 0.16 | |
| Ethnicity‡ | | | | 0.84 | | | 0.28 |
| Caucasian | 39 | 1.00 (Reference) | 0.57 ± 0.09 | | 1.00 (Reference) | 0.43 ± 0.08 | |
| Other | 10 | 1.10 (0.41, 2.95) | 0.52 ± 0.16 | | 1.53 (0.68, 3.46) | 0.20 ± 0.13 | |
| Tumor stage | | | | 0.42 | | | 0.032 |
| Ta | 10 | 1.00 (Reference) | 0.56 ± 0.17 | | 1.00 (Reference) | 0.63 ± | |

Figure 3B.

| | | | | | | |
|---|---|---|---|---|---|---|
| T1-T2 | 21 | 0.77 (0.25, 2.36) | 0.52 ± 0.14 | | 2.07 (0.67, 6.38) | 0.17 ± 0.37 |
| T3-T4 | 27 | 1.34 (0.49, 3.67) | 0.58 ± 0.10 | | 3.16 (1.07, 9.32) | 0.11 ± 0.30 0.09 |
| Pathologic stage | | | | 0.22 | | 0.050 |
| Noninvasive (Ta, N-) | 10 | 1.00 (Reference) | 0.56 ± 0.17 | | 1.00 (Reference) | 0.63 ± 0.17 |
| Organ confined, invasive (T1/2, N-) | 17 | 0.87 (0.28, 2.75) | 0.58 ± 0.16 | | 2.21 (0.70, 6.95) | 0.34 ± 0.12 |
| Extravesical extension (T3/4, N-) | 11 | 0.53 (0.13, 2.19) | 0.18 ± 0.12 | | 2.06 (0.60, 7.05) | 0.45 ± 0.15 |
| Nodal metastases (any T, N+) | 20 | 1.62 (0.58, 4.53) | 0.71 ± 0.10 | | 3.55 (1.16, 10.84) | 0.25 ± 0.10 |
| Lymph node density[§] | | | | <0.001 | | <0.001 |
| 0 (37.5[¶]) | 38 | 1.00 (Reference) | 0.48 ± 0.11 | | 1.00 (Reference) | 0.46 ± 0.09 |
| 0.1-10% (49.4[¶]) | 10 | 0.89 (0.30, 2.61) | 0.40 ± 0.15 | | 0.99 (0.38, 2.60) | 0.50 ± 0.16 |
| >10% (32.5[¶]) | 10 | 4.19 (1.76, 10.01) | 1.00 | | 4.51 (1.91, 10.64) | 1.00 |
| Tumor grade[∫] | | | | 0.27 | | 0.050 |
| Low | 11 | 1.00 (Reference) | 0.44 ± 0.17 | | 1.00 (Reference) | 0.59 ± 0.16 |

Figure 3C.

| | | | | | |
|---|---|---|---|---|---|
| High | 47 | 1.79 (0.62, 5.15) | 0.59 ± 0.08 | 2.38 (0.88, 6.43) | 0.34 ± 0.07 |

\* Based on the log-rank test.
† Greenwood SE.
‡ The ethnic background of 9 subjects was unavailable.
§ Percentage of dissected lymph nodes that were positive for metastasis.
¶ Mean number of lymph nodes dissected.
ʲ Based on the Bergkvist grading system.
Abbreviations: CI, confidence interval; SE, standard error.

Figure 4A.

| Gene | n* | Recurrence | | Overall survival | |
|---|---|---|---|---|---|
| | | Relative risk of recurring (95% CI) | P value | Relative risk of dying (95% CI) | P value |
| *MAPK12* | | | 0.091 | | <0.001† |
| Normal | 17 | 1.00 (Reference) | | 1.00 (Reference) | |
| Low | 24 | 0.39 (0.15, 0.97) | | 0.23 (0.10, 0.53) | |
| High | 17 | 0.73 (0.30, 1.80) | | 0.55 (0.25, 1.23) | |
| *JUN* | | | 0.026† | | 0.001† |
| Normal | 40 | 1.00 (Reference) | | 1.00 (Reference) | |
| Low | 3 | 0.79 (0.11, 5.82) | | 0.49 (0.07, 3.61) | |
| High | 10 | 2.97 (1.18, 7.47) | | 3.41 (1.50, 7.75) | |
| *TNFSF10* | | | 0.291 | | 0.007† |
| Normal | 33 | 1.00 (Reference) | | 1.00 (Reference) | |
| Low | 9 | 0.49 (0.14, 1.65) | | 0.50 (0.17, 1.48) | |
| High | 14 | 1.36 (0.58, 3.18) | | 2.05 (0.99, 4.25) | |
| *STAT3* | | | 0.009† | | 0.050† |
| Normal | 29 | 1.00 (Reference) | | 1.00 (Reference) | |
| Low | 11 | 3.31 (1.24, 8.81) | | 1.87 (0.79, 4.40) | |
| High | 16 | 3.08 (1.27, 7.47) | | 2.38 (1.12, 5.09) | |
| *CCNA2* | | | 0.540 | | 0.009† |
| Normal | 51 | 1.00 (Reference) | | 1.00 (Reference) | |
| Low | 2 | 0.55 (0.07, 4.02) | | 0.40 (0.06, 2.83) | |

Figure 4B.

| | | | | | |
|---|---|---|---|---|---|
| High | 2 | 2.39 (0.30, 18.99) | | 6.03 (1.27, 28.74) | 0.014‡ |
| *ICAM1* | | | 0.338 | | |
| Normal | 17 | 1.00 (Reference) | | 1.00 (Reference) | |
| Low | 19 | 0.78 (0.29, 2.07) | | 0.67 (0.26, 1.70) | |
| High | 20 | 1.48 (0.60, 3.64) | | 1.87 (0.82, 4.26) | |
| *BCL2L1* | | | 0.204 | | 0.015‡ |
| Normal | 6 | 1.00 (Reference) | | 1.00 (Reference) | |
| Low | 8 | 0.32 (0.06, 1.72) | | 0.12 (0.01, 1.04) | |
| High | 42 | 1.08 (0.37, 3.13) | | 1.28 (0.48, 3.40) | |
| *MAP2K6* | | | 0.044† | | 0.016‡ |
| Normal | 12 | 1.00 (Reference) | | 1.00 (Reference) | |
| Low | 22 | 0.42 (0.15, 1.18) | | 0.59 (0.23, 1.53) | |
| High | 24 | 1.15 (0.46, 2.89) | | 1.58 (0.65, 3.82) | |
| *IGF1* | | | 0.021† | | 0.147 |
| Normal | 17 | 1.00 (Reference) | | 1.00 (Reference) | |
| Low | 29 | 1.13 (0.47, 2.71) | | 1.15 (0.51, 2.57) | |
| High | 4 | 4.95 (1.15, 21.32) | | 2.93 (0.88, 9.77) | |
| *SOD1* | | | 0.033† | | 0.081 |
| Normal | 9 | 1.00 (Reference) | | 1.00 (Reference) | |
| Low | 8 | 2.04 (0.62, 6.76) | | 3.03 (0.89, 10.31) | |
| High | 34 | 0.62 (0.24, 1.61) | | 1.52 (0.55, 4.21) | |
| *TGIF* | | | 0.449 | | 0.047‡ |
| Normal | 31 | 1.00 (Reference) | | 1.00 (Reference) | |
| Low | 9 | 0.96 (0.35, 2.65) | | 0.81 (0.31, 2.10) | |
| High | 18 | 1.62 (0.69, 3.82) | | 2.04 (0.98, 4.28) | |
| *FOSL1* | | | 0.337 | | 0.051‡‡ |

Figure 4C.

|  |  |  |  |  |
|---|---|---|---|---|
| Normal | 22 | 1.00 (Reference) | | 1.00 (Reference) |
| Low | 26 | 1.69 (0.75, 3.77) | | 1.09 (0.53, 2.26) |
| High | 8 | 1.95 (0.60, 6.36) | | 2.75 (1.08, 7.03) |
| *BCL2* | | | 0.055‡ | 0.197 |
| Normal | 24 | 1.00 (Reference) | | 1.00 (Reference) |
| Low | 25 | 0.45 (0.19, 1.07) | | 0.61 (0.29, 1.30) |
| High | 9 | 1.40 (0.56, 3.51) | | 1.23 (0.51, 2.95) |

\* Only includes subjects where respective gene expression values were available.
† Statistically significant ($P \leq 0.050$).
‡ Trend towards significance ($0.050 < P \leq 0.055$).

Abbreviations: CI, confidence interval.

Figure 5A.

| | n | Recurrence | | | Disease-specific Survival | | | Overall Survival | | |
|---|---|---|---|---|---|---|---|---|---|---|
| | | Relative Risk of recurring (95% CI) | Probability ± SE† of 5-year recurrence | P value | Relative Risk of dying (95% CI) | Probability ± SE† of 5-year survival | P value | Relative Risk of dying (95% CI) | Probability ± SE† of 5-year survival | P value |
| Favorable§ expression of ≥3/4 genes | 35 | 1.00 (Reference) | 0.41 ± 0.09 | | 1.00 (Reference) | 0.68 ± 0.08 | | 1.00 (Reference) | 0.61 ± 0.09 | |
| Favorable§ expression of ≤2/4 genes | 21 | 3.22 (1.46, 7.13)* | 0.88 ± 0.10 | <0.001* | 4.13 (1.83, 9.32) | 0.07 ± 0.07 | <0.001* | 4.10 (2.00, 8.41)* | 0.05 ± 0.05 | <0.001* |
| Favorable§ expression of ≥3/4 genes | 35 | 1.00 (Reference) | - | | 1.00 (Reference) | - | | 1.00 (Reference) | - | |
| Favorable§ expression of ≤2/4 genes | 21 | 3.09 (1.37, 6.95)¶ | - | 0.007¶ | 4.11 (1.75, 9.63)¶ | - | 0.001¶ | 4.48 (2.09, 9.62)¶ | - | <0.001¶ |
| Favorable§ expression of ≥3/4 genes | 35 | 1.00 (Reference) | - | | 1.00 (Reference) | - | | 1.00 (Reference) | - | |

Figure 5B.

| | | | | | | | |
|---|---|---|---|---|---|---|---|
| Favorable§ expression of ≤2/4 genes | 21 | 2.63 (1.11, 6.25)ʲ | - | 0.02 | 3.92 (1.59, 9.66)ʲ | 8ʲ | - | 0.003ʲ | 4.11 (1.89, 8.95)ʲ | - | <0.001ʲ |

‡ 2 subjects had two favorable, one unfavorable and one missing gene expression value, and could thus not be confidently classified into either group, and were excluded for this analysis.
§ Favorable was defined as low or normal expression of the gene compared to normal urothelium.
\* Based on the log-rank test.
† Greenwood SE.
¶ Based on Cox Proportional hazards model, stratified by pathologic stage.
ʲ Based on Cox Proportional hazards model, stratified by lymph node density.
Abbreviations: CI, confidence interval; SE, standard error.

Figure 6A.

| | n | Disease-specific survival | |
|---|---|---|---|
| | | Relative Risk of Dying (95% CI)* | P value* |
| Validation cohort | 91 | | |
| Age | | | 0.54 |
| ≤69 years | 52 | 1.00 (Reference) | |
| ≥70 years | 39 | 0.85 (0.50, 1.44) | |
| Sex | | | 0.34 |
| Male | 63 | 1.00 (Reference) | |
| Female | 28 | 0.75 (0.41, 1.38) | |
| Tumor stage | | | <0.001 |
| Ta, T1-T2 | 35 | 1.00 (Reference) | |
| T3-T4 | 56 | 3.88 (1.67, 9.02) | |
| Pathologic stage | | | <0.001 |
| Organ confined (Ta/1/2, N-) | 35 | 1.00 (Reference) | |
| Extravesical extension (T3/4, N-) | 31 | 3.39 (1.39, 8.24) | |
| Nodal metastases (any T, N+) | 25 | 4.48 (1.89, 10.62) | |
| Tumor grade | | | 0.001 |
| Grade 2 | 18 | 1.00 (Reference) | |
| Grade 3 | 73 | 8.63 (1.27, 58.85) | |

Figure 6B.

| | | | |
|---|---|---|---|
| 11-gene predictive panel for survival¶ | | | 0.007 |
| Favorable$ expression of ≥7/11 genes | 56 | 1.00 (Reference) | |
| Favorable$ expression of ≤6/11 genes | 35 | 2.00 (1.21, 3.31) | |
| 4-gene predictive panel for outcome‡ | | | 0.039 |
| Favorable$ expression of ≥3/4 genes | 50 | 1.00 (Reference) | |
| Favorable$ expression of ≤2/4 genes | 41 | 1.71 (1.02, 2.87) | |

\* Based on the Pearson's chi-square test.

$ Favorable was defined as low expression of the gene in the tumor (in all duplicates, if applicable).

¶ *MAPK12, JUN, TNFSF10, CCNA2, ICAM1, BCL2L1, MAP2K6, TGIF, STAT3, FOSL1,* and *GSTM3.*

‡ *JUN, MAP2K6, STAT3,* and *ICAM1.*

Abbreviations: CI, confidence interval.

Figure 7A.

| Gene | Official Name | GeneID | Transcribed protein |
|---|---|---|---|
| APOPTOSIS | | | |
| ANXA5 | annexin A5 | 308 | Annexin V |
| BAD | BCL2-antagonist of cell death | 572 | BAD |
| BCL2 | B-cell CLL/lymphoma 2 | 596 | Bcl-2 |
| BCL2L1 | BCL2-like 1 | 598 | Bcl-XL |
| CYP1A2 | cytochrome P450, family 1, subfamily A, polypeptide 2 | 1544 | CYP1A2 |
| DAP | death-associated protein | 1611 | DAP1 |
| PTGS2 | prostaglandin-endoperoxide synthase 2 (prostaglandin G/H synthase and cyclooxygenase) | 5743 | COX-2 |
| TGFBR2 | transforming growth factor, beta receptor II (70/80kDa) | 7048 | TGF-beta receptor type II |
| TGIF | TGFB-induced factor (TALE family homeobox) | 7050 | TGIF |
| TNF | tumor necrosis factor (TNF superfamily, member 2) | 7124 | TNF-alpha |
| TNFAIP1 | tumor necrosis factor, | 7126 | TNFAIP1 |

Figure 7B.

| Gene | Official Name | GeneID | Transcribed protein |
|---|---|---|---|
| | alpha-induced protein 1 (endothelial) | | |
| TNFRSF1A | tumor necrosis factor receptor superfamily, member 1A | 7132 | TNF-R1 |
| TNFSF10 | tumor necrosis factor (ligand) superfamily, member 10 | 8743 | Apo-2L |
| TRAF4 | TNF receptor-associated factor 4 | 9618 | TRAF4 |

| Gene | Official Name | GeneID | Transcribed protein |
|---|---|---|---|
| CELL CYCLE | | | |
| CCNA2 | cyclin A2 | 890 | Cyclin A2 |
| CCND3 | cyclin D3 | 896 | Cyclin D3 |
| CCNE1 | cyclin E1 | 898 | Cyclin E |
| CCNG1 | cyclin G1 | 900 | Cyclin G1 |
| CDC2 | cell division cycle 2, G1 to S and G2 to M | 983 | CDK1 (p34) |
| CDC25C | cell division cycle 25C | 995 | CDC25C |
| CDK7 | cyclin-dependent kinase 7 (MO15 homolog, Xenopus laevis, | 1022 | CDK7 |

Figure 7C.

| Gene | Description | ID | Protein |
|---|---|---|---|
| CDK8 | cdk-activating kinase) cyclin-dependent kinase 8 | 1024 | CDK8 |
| PCNA | proliferating cell nuclear antigen | 5111 | PCNA |
| GENE REGULATION | | | |
| FOS | v-fos FBJ murine osteosarcoma viral oncogene homolog | 2353 | c-Fos |
| FOSL1 | FOS-like antigen 1 | 8061 | Fra-1 |
| HSF1 | heat shock transcription factor 1 | 3297 | HSF1 |
| JUN | v-jun sarcoma virus 17 oncogene homolog (avian) | 3725 | c-Jun |
| JUNB | jun B proto-oncogene | 3726 | JunB |
| MAP3K14 | mitogen-activated protein kinase kinase kinase 14 | 9020 | NIK (MAP3K14) |
| MYC | v-myc | 4609 | c-Myc |

Figure 7D.

| | | | |
|---|---|---|---|
| NFKB1 | myelocytomatosis viral oncogene homolog (avian) nuclear factor of kappa light polypeptide gene enhancer in B-cells 1 (p105) | 4790 | NF-kB1 |
| SP1 | Sp1 transcription factor | 6667 | SP1 |

| Gene | Official Name | GeneID | Transcribed protein |
|---|---|---|---|
| APOPTOSIS + CELL CYCLE | | | |
| CDKN1A | cyclin-dependent kinase inhibitor 1A (p21, Cip1) | 1026 | p21 |
| CDKN1B | cyclin-dependent kinase inhibitor 1B (p27, Kip1) | 1027 | p27KIP1 |
| CDKN2A | cyclin-dependent kinase inhibitor 2A (melanoma, p16, inhibits CDK4) | 1029 | p14ARF |
| CDKN2C | cyclin-dependent kinase inhibitor 2C (p18, inhibits CDK4) | 1031 | p18 |
| GAPDH | glyceraldehyde-3-phosphate dehydrogenase | 2597 | GAPDH |

Figure 7E.

| | | | |
|---|---|---|---|
| MXD1 | MAX dimerization protein 1 | 4084 | MAD |
| RB1 | retinoblastoma 1 (including osteosarcoma) | 5925 | Rb protein |
| RBL2 | retinoblastoma-like 2 (p130) | 5934 | p130 |
| TP53 | tumor protein p53 (Li-Fraumeni syndrome) | 7157 | p53 |

APOPTOSIS + CELL CYCLE + GENE REGULATION

| | | | |
|---|---|---|---|
| E2F1 | E2F transcription factor 1 | 1869 | E2F1 |
| E2F2 | E2F transcription factor 2 | 1870 | E2F2 |
| E2F4 | E2F transcription factor 4, p107/p130-binding | 1874 | E2F4 |
| E2F5 | E2F transcription factor 5, p130-binding | 1875 | E2F5 |

| Gene | Official Name | GeneID | Transcribed protein |
|---|---|---|---|
| ANTI-OXIDATION | | | |
| GSTM3 | glutathione S-transferase M3 (brain) | 2947 | GSTM3 |
| GSTP1 | glutathione S-transferase pi | 2950 | GSTP1 |
| GSTT1 | glutathione S-transferase theta 1 | 2952 | GSTT1 |
| SOD1 | superoxide dismutase 1, | 6647 | SOD1 |

Figure 7F.

CELL GROWTH REGULATION

| | | | |
|---|---|---|---|
| IGF1 | soluble (amyotrophic lateral sclerosis 1 (adult)) | | |
| IGF1 | insulin-like growth factor 1 (somatomedin C) | 3479 | IGF1 |
| IGF2R | insulin-like growth factor 2 receptor | 3482 | IGF-2 receptor |
| PDGFB | platelet-derived growth factor beta polypeptide (simian sarcoma viral (v-sis) oncogene homolog) | 5155 | PDGF-B |
| PDGFRL | platelet-derived growth factor receptor-like | 5157 | PDGFRL |

SIGNAL TRANSDUCTION

| | | | |
|---|---|---|---|
| ERBB2 | v-erb-b2 erythroblastic leukemia viral oncogene homolog 2, neuro/glioblastoma derived oncogene homolog (avian) | 2064 | ErbB2 |
| LYN | v-yes-1 Yamaguchi sarcoma viral related oncogene homolog | 4067 | Lyn |
| MAPK8 | mitogen-activated protein kinase 8 | 5599 | JNK1 (MAPK8) |
| MAPK9 | mitogen-activated protein kinase 9 | 5601 | JNK2 (MAPK9) |

Figure 7G.

| | | | |
|---|---|---|---|
| MAPK12 | mitogen-activated protein kinase 12 | 6300 | p38gamma (MAPK12) |
| MAP2K6 | mitogen-activated protein kinase kinase 6 | 5608 | MEK6 (MAP2K6) |
| STAT3 | signal transducer and activator of transcription 3 (acute-phase response factor) | 6774 | STAT3 |

| Gene | Official Name | GeneID | Transcribed protein |
|---|---|---|---|
| ANGIOGENESIS | | | |
| FGF5 | fibroblast growth factor 5 | 2250 | FGF5 |
| FGFR4 | fibroblast growth factor receptor 4 | 2264 | FGFR4 |
| KDR | kinase insert domain receptor (a type III receptor tyrosine kinase) | 3791 | VEGFR-2 |
| VEGF | vascular endothelial growth factor | 7422 | VEGF-A |
| INVASION | | | |
| BMP6 | bone morphogenetic protein 6 | 654 | BMP6 |
| CDH3 | cadherin 3, type 1, P-cadherin (placental) | 1001 | P-cadherin |

Figure 7H.

| | | | |
|---|---|---|---|
| *ICAM1* | intercellular adhesion molecule 1 (CD54), human rhinovirus receptor | 3383 | ICAM1 |
| *MMP16* | matrix metallopeptidase 16 (membrane-inserted) | 4325 | MMP-16 |
| *TIMP2* | TIMP metallopeptidase inhibitor 2 | 7077 | TIMP2 |
| REFERENCE GENE | | | |
| *ACTB* | actin, beta | 60 | β-actin |

Figure 8A.

| Gene | Prognostic for | | Expression value (compared to normal urothelium) | | |
|---|---|---|---|---|---|
| | Recurrence | Overall survival | Low | Normal | High |
| MAPK12 | | Y | | | |
| JUN | Y | Y | | | |
| TNFSF10 | | Y | | | |
| CCNA2 | | Y | | | |
| STAT3 | Y | Y | | | |
| ICAM1 | Y | Y | | | |
| BCL2L1 | | Y | | | |
| MAP2K6 | Y | Y | | | |
| IGF1 | Y | | | | |
| SOD1 | Y | | | | |
| TGIF | | Y | | | |
| FOSL1 | | Y† | | | |
| BCL2 | Y† | | | | |
| BMP6 | Y | | | | |
| GSTM3 | | Y | | | |

Y indicates selection of the gene by log-rank and/or recursive partitioning analyses.
† indicates trend towards statistical significance.

Genes in bold were selected for the common 4-gene panel.

Favorable expression

Unfavorable expression

Figure 9.

| Gene | Log-rank P value (univariate analysis)*, confirmed by bootstrap | | Recursive partitioning (multivariable) analysis | |
|---|---|---|---|---|
| | Recurrence | Overall survival | Recurrence | Overall survival |
| MAPK12 | | <0.001 | | Y |
| JUN | 0.026 | 0.001 | | |
| TNFSF10 | | 0.007 | | |
| STAT3 | 0.009 | 0.050 | | |
| CCNA2 | | 0.009 | | |
| ICAM1 | | 0.014 | Y | Y |
| BCL2L1 | | 0.015 | | |
| MAP2K6 | 0.044 | 0.016 | | |
| IGF1 | 0.021 | | Y | |
| SOD1 | 0.033 | | | |
| TGIF | | 0.047 | Y | |
| BMP6 | | | | Y |
| GSTM3 | | | | |

* only P≤0.050 shown
Y indicates gene predictive of recurrence and/or overall survival by recursive partitioning analysis. JUN, STAT3, ICAM1 and MAP2K6 were able to significantly predict recurrence and overall survival by log-rank and/or recursive partitioning analysis and were thus selected for the common 4-gene panel.

US 8,293,880 B2

PROGNOSTIC PANEL FOR URINARY BLADDER CANCER

The present application claims the benefit of priority under 35 U.S.C. §119(e) of provisional application Ser. No. 61/039,351, filed Mar. 25, 2008, the contents of which are hereby incorporated by reference.

GOVERNMENT RIGHTS

This invention was made with U.S. Government support on behalf of the National Institutes of Health grant CA-86871 and National Cancer Institute grant CA-14089. The U.S. Government may have certain rights in this invention.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cancer of the urothelial layer is the most common type of urinary bladder tumor and is four times more common in men than in women. Approximately 68,810 new cases of urothelial carcinoma (CC) were detected in 2008 in the United States, and an estimated 14,100 patients died of the disease. Current UC management primarily depends on the histologic grading and pathologic staging of the tumor[1,2]. While these provide an assessment of risk, they are unable to predict the outcome for an individual patient. Molecular alterations in tumors precede visually identifiable morphologic changes and are responsible for their biologic behavior[3,4], prognosis, and response to therapy. Hence, histopathologic staging in UC needs to be complemented with molecular correlates to accurately predict clinical outcome and therapeutic response.

SUMMARY OF THE INVENTION

Various embodiments described herein include a kit for prognostic use, comprising a single prognostic panel consisting essentially of two, three or four of the following markers: v-jun sarcoma virus 17 oncogene homolog (JUN), mitogen-activated protein kinase 6 (MAP2K6), signal transducer and activator of transcription 3 (STAT3), and intercellular adhesion molecule 1 (ICAM1). In another embodiment, the single prognostic panel consists essentially of three or four of the following markers: JUN, MAP2K6, STAT3, and ICAM1. In another embodiment, the single prognostic panel consists essentially of the following markers: JUN, MAP2K6, STAT3, and ICAM1. In another embodiment, the kit further comprises reference markers, detection and amplification reagents for detecting the presence of markers and/or instructions for using the single prognostic panel.

Other embodiments include methods of determining a prognosis of cancer characterized by disease recurrence despite possible future treatment with definitive surgery in an individual, comprising determining the presence or absence of a high level of expression in the individual relative to a normal baseline standard of at least two of the following markers, JUN, MAP2K6, STAT3, and ICAM1, and prognosing a case of cancer characterized by disease recurrence despite possible future treatment with definitive surgery if the individual demonstrates the presence of a high level of expression relative to a normal baseline standard of at least two of the markers. In another embodiment, the presence of four of said markers presents a greater likelihood of a prognosis of cancer characterized by disease recurrence despite possible future treatment with definitive surgery than the presence of three or two of said markers, and the presence of three of said markers presents a greater likelihood of a prognosis of cancer characterized by disease recurrence despite possible future treatment with definitive surgery than the presence of two of said markers but less than the presence of four of said markers, and the presence of two of said markers presents a greater likelihood of a prognosis of cancer characterized by disease recurrence despite possible future treatment with definitive surgery than the presence of one or none of said markers but less than the presence of three or four of said markers. In another embodiment, the cancer is urothelial carcinoma. In another embodiment, the cancer is brain cancer, thyroid cancer, breast cancer, lung cancer, ovarian cancer, pituitary cancer and/or colon cancer.

Other embodiments include methods of treating cancer characterized by disease recurrence despite possible future treatment with definitive surgery in an individual, comprising determining the presence or absence of a high level of expression in the individual relative to a normal baseline standard of at least two of the following markers: JUN, MAP2K6, STAT3, and ICAM1, prognosing a case of cancer characterized by disease recurrence despite possible future treatment with definitive surgery if the individual demonstrates the presence of a high level of expression relative to a normal baseline standard of at least two of the risk markers, and treating the cancer with a non-surgical treatment if the individual has a prognosis of a case of cancer characterized by disease recurrence despite possible future treatment with definitive surgery. In another embodiment, the non-surgical treatment comprises chemotherapy.

Various embodiments include a kit for prognostic use, comprising a single prognostic panel consisting essentially of six, seven, eight, nine, ten or eleven of the following markers: JUN, MAP2K6, STAT3, ICAM1, insulin-like growth factor 1 (IGF1), superoxide dismutase 1(SOD1), B-cell lymphoma 2 (BCL2), bone morphogenetic protein 6 (BMP6), mitogen-activated protein kinase 12 (MAPK12), tumor necrosis factor superfamily member 10 (TNFSF10), cyclin A2 (CCNA2), BCL2-like I (BCL2L1), transforming growth factor-beta-induced factor (TGIF), FOS-like antigen 1 (FOSL1) and glutathione S-transferase M3 (GSTM3), where four of the markers consist essentially of the following markers: JUN, MAP2K6, STAT3, ICAM1. In another embodiment, the single prognostic panel consists essentially of six, seven or eight of the following markers: JUN, MAP2K6, STAT3, ICAM1, IGF1, SOD1, BCL2, and BMP6. In another embodiment, the single prognostic panel consists essentially of six, seven, eight, nine, ten or eleven of the following markers: JUN, MAP2K6, STAT3, ICAM1, MAPK12, TNFSF10, CCNA2, BCL2L1, TGIF, FOSL1, and GSTM3.

Other embodiments include methods of determining a prognosis of cancer characterized by disease recurrence despite possible future treatment with definitive surgery in an individual, comprising determining the presence or absence of a high level of expression in the individual relative to a normal baseline standard of one or more of the following markers: JUN, MAP2K6, STAT3, ICAM1, IGF1, SOD1, BCL2, BMP6, MAPK12, TNFSF10, CCNA2, BCL2 L1, TGIF, FOSL1 and GSTM3, and prognosing a case of cancer characterized by disease recurrence despite possible future treatment with definitive surgery if the individual demonstrates the presence of a high level of expression relative to a normal baseline standard of one or more of the markers.

Other features and advantages of the invention will become apparent from the following detailed description, taken in conjunction with the accompanying drawings, which illustrate, by way of example, various embodiments of the invention.

BRIEF DESCRIPTION OF THE FIGURES

FIG. 3 depicts, in accordance with an embodiment herein, an association between demographics and clinicopathologic parameters, and outcome.

FIG. 4 depicts, in accordance with an embodiment herein, genes predictive of recurrence and overall survival by univariate (log-rank) analysis.

FIG. 5 depicts, in accordance with an embodiment herein, association between favorable (low or normal) expression of JUN, MAP2K6, STAT3 and ICAM1, and outcome.

FIG. 6 depicts, in accordance with an embodiment herein, association between demographics, clinicopathologic parameters and prognostic gene panels, and disease-specific survival in the external validation cohort.

FIG. 7 depicts, in accordance with an embodiment herein, a list of genes involved in eight crucial tumorigenic pathways investigated using StaRT-PCR including their GeneID and protein transcribed.

FIG. 9 depicts, in accordance with an embodiment herein, a list of genes of interest from univariate and recursive partitioning analyses

DESCRIPTION OF THE INVENTION

Figure 1:
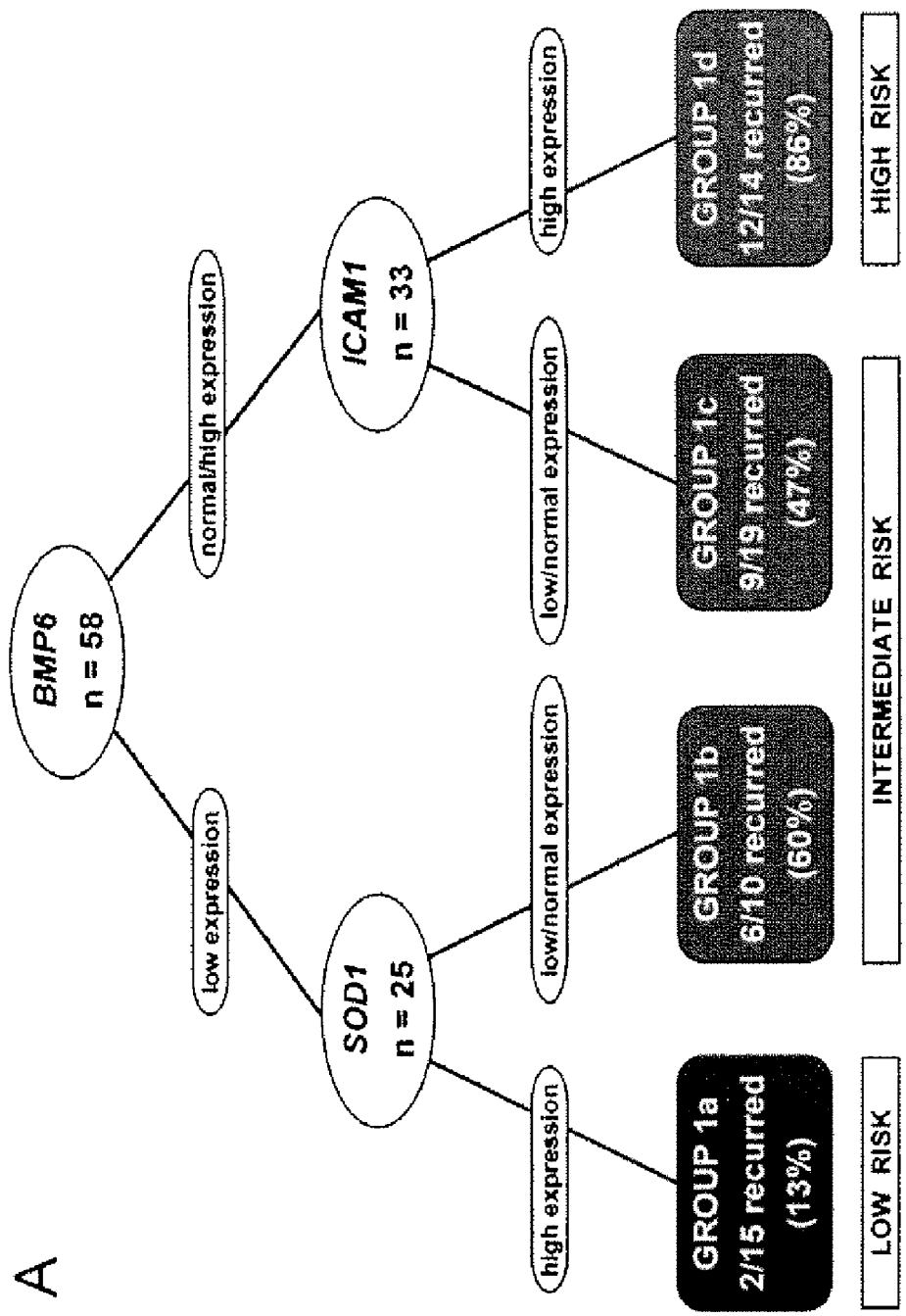
FIG. 1 depicts, in accordance with an embodiment herein, recursive partitioning analysis for clinical outcome in urothelial carcinoma. (A) Expression values of BIP6, SOD1 and ICAM1 were used to define four distinct patient groups 1a-1d based on their time to recurrence that had (B) significant differences in their risk of recurring. (C) Similarly, expression values of MAPK12, GSTV3 and ICAM1 were used to define four distinct patient groups 2a-2d based on their overall survival that had (D) significant differences in their survival risk.
Figure 1:
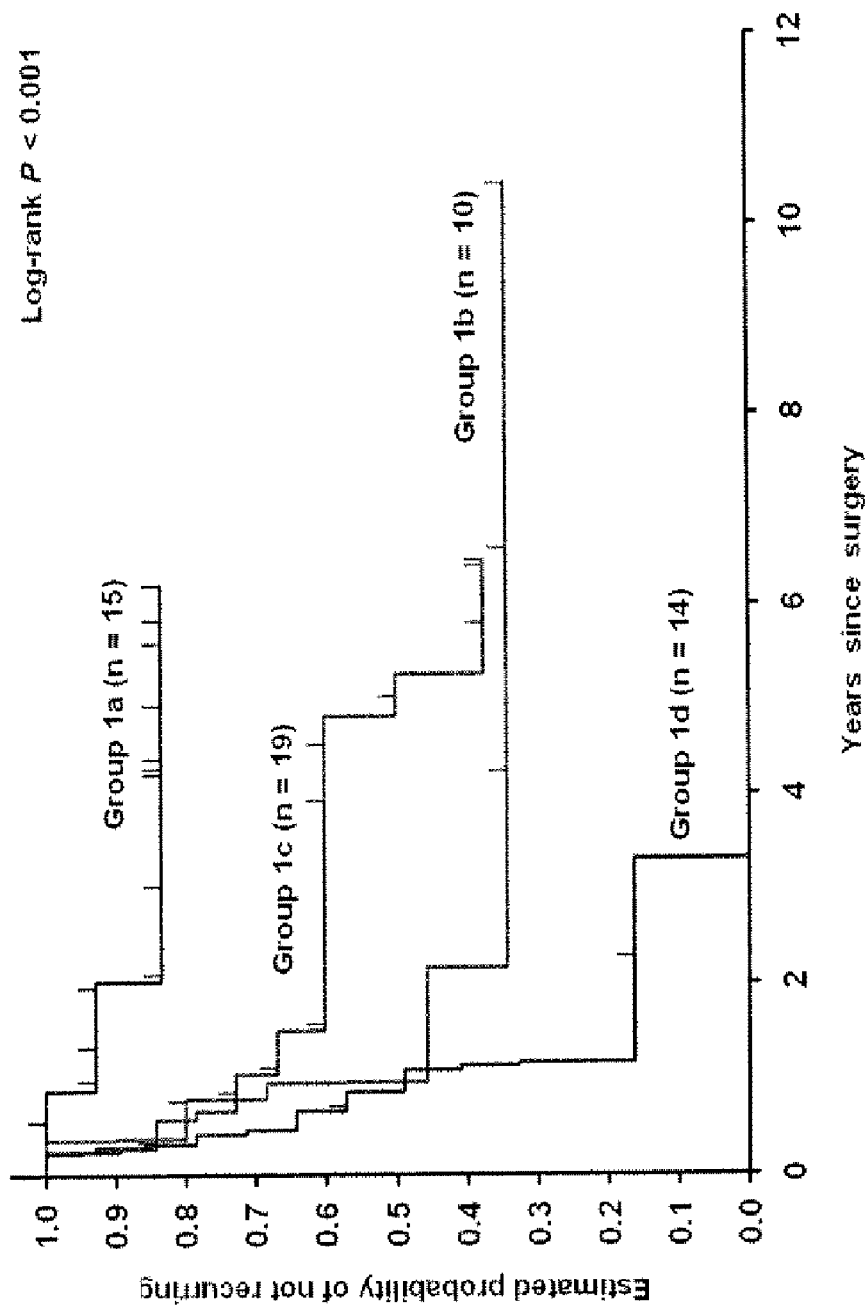
Figure 1:
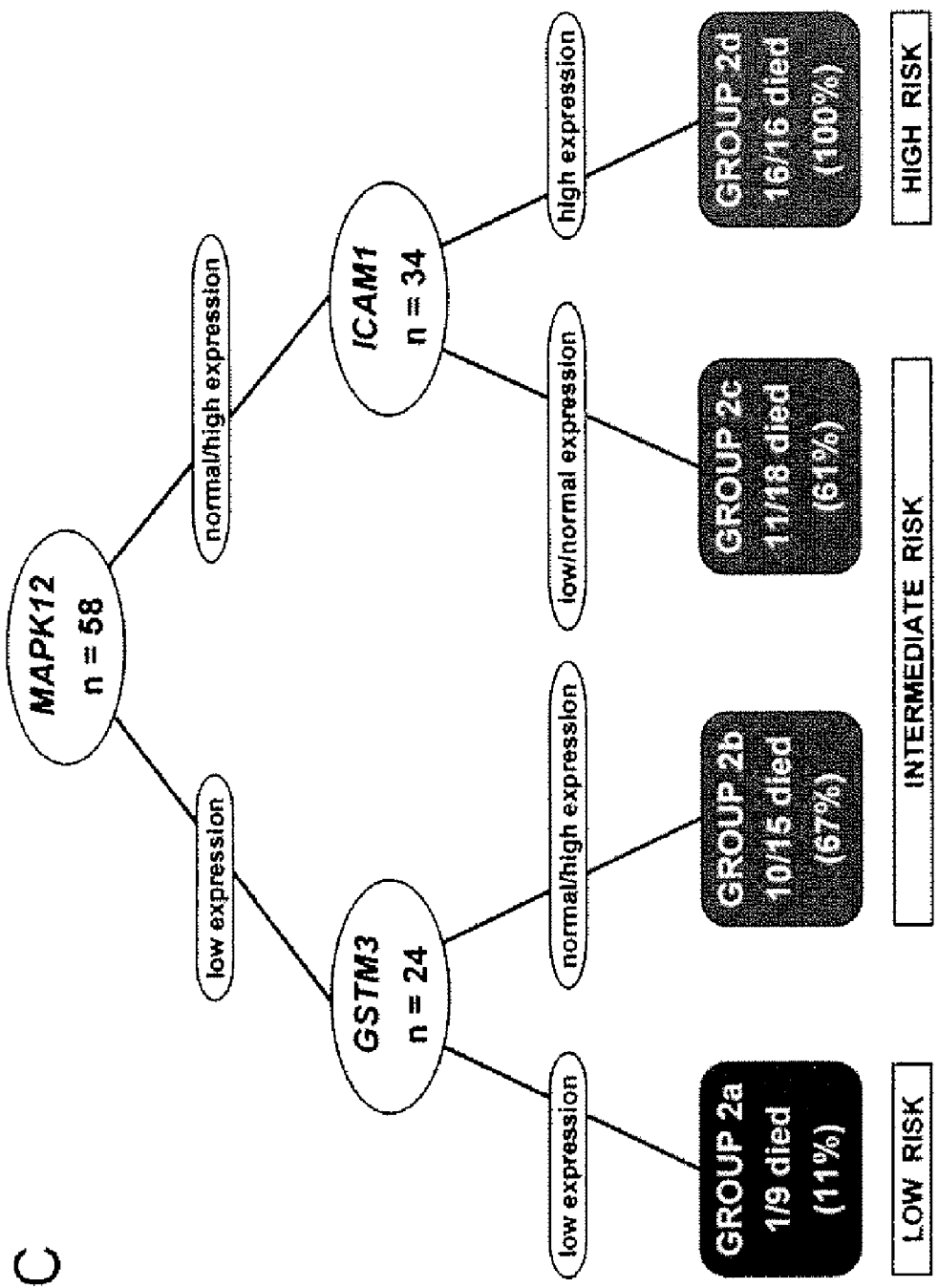
Figure 1:
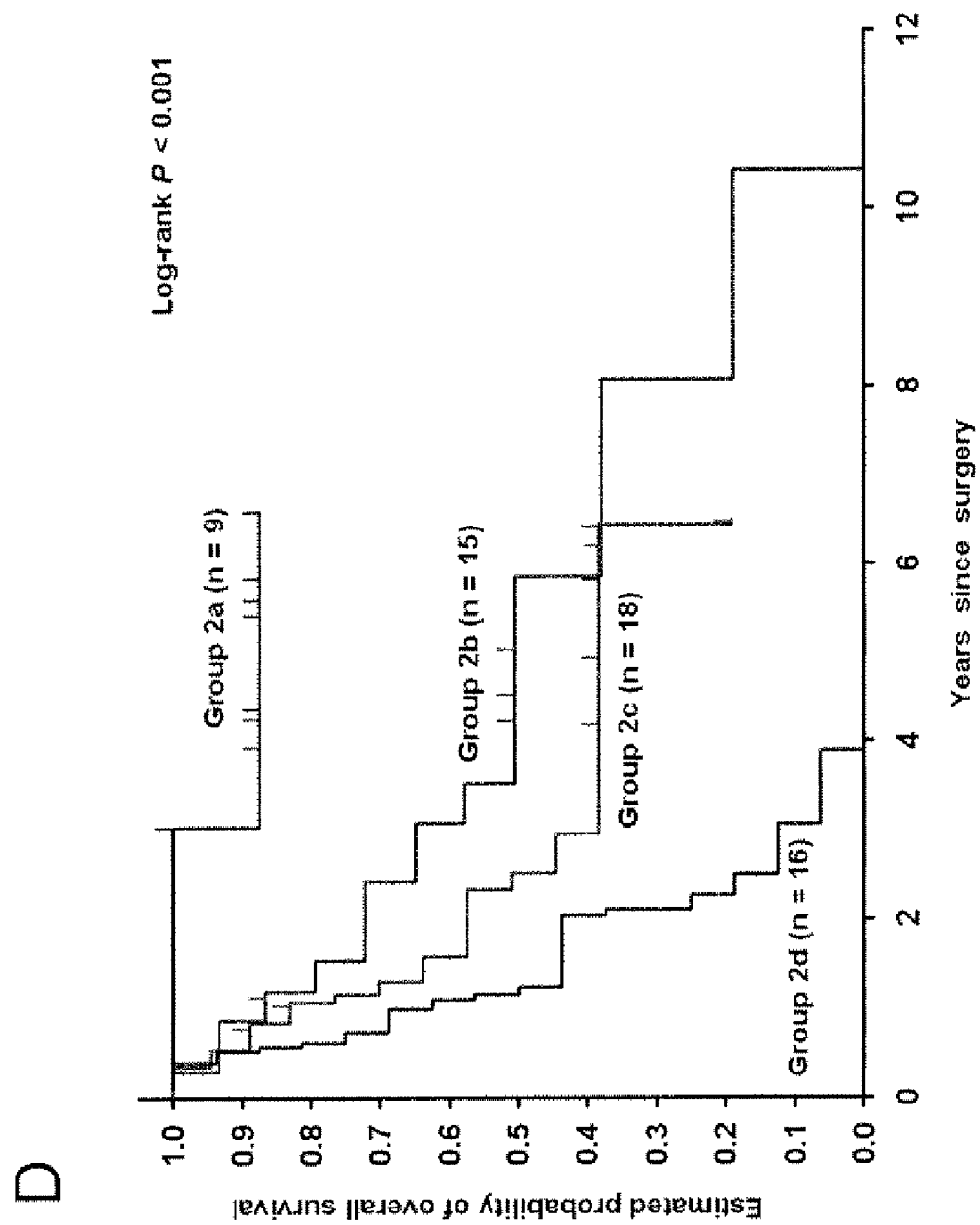

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed, J. Wiley & Sons (New York, N.Y. 2001); March, *Advanced Organic Chemistry Reactions, Mechanisms and Structure* 5$^{th}$ ed, J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention indeed, the present invention is in no way limited to the methods and materials described.

As used herein, the designations of "normal," "low," and "high" gene or marker expression levels are determined relative to a normal baseline standard of gene or marker expression level.

There are various methods known to one of skill in the art in determining the "normal baseline standard" of expression level. For example, as described herein, the inventors used true normal urothelium to obtain normal baseline standard expression levels.

Levels of gene or marker expression can be determined using various methods known to one of skill in the art. For example, as described herein, the inventors used a standardized competitive reverse transcriptase—polymerase chain reaction (StaRT-PCR) approach to quantify absolute expressions of genes in relation to a fixed quantity of the housekeeping gene β-actin. Similarly, as readily apparent to one of skill in the art, detection and quantification of various compositions that might include polynucleotides, polypeptides as well as various reporter molecules may be used to aid in determining levels of gene or marker expression.

As used herein, the term "UC" means urothelial carcinoma, which is also known as bladder cancer.

As used herein, the term "StaRT-PCR" means standardized competitive reverse transcriptase—polymerase chain reaction.

As used herein, the term "RP" means recursive partitioning.

As used herein, the term "AIC" means Akaike information criterion.

As used herein, the term "TRAIL" means tumor necrosis factor-related apoptosis-inducing ligand.

As used herein, the term "CT" means competitive template.

As used herein, the term "definitive surgery" means surgery where all of the known tumor is removed.

As disclosed herein, with growing evidence that multiple alterations in major cancer pathways are responsible for UC progression[5], the inventors profiled the expression of genes involved in crucial cancer pathways by standardized competitive reverse transcriptase-polymerase chain reaction (StaRT-PCR), quantifying absolute expressions in relation to a fixed quantity of the housekeeping gene β-actin[6]. The inventors sought to determine if alterations in molecular pathways could supplement TNM staging in order to more accurately predict clinical outcome in patients with urothelial carcinoma (UC).

As further disclosed herein, expression of 69 genes involved in known cancer pathways were quantified from bladder specimens from 58 UC patients (stages Ta-T4) and 5 normal urothelium controls. All tumor transcript values beyond two standard deviations from the normal mean expression were designated as over or underexpressed. Univariate and multivariable analyses were conducted to obtain a predictive expression signature. A published external dataset was used to confirm the potential of the prognostic gene panels.

As further disclosed herein, six and ten genes were significantly associated with time to recurrence and overall survival by univariate analysis, respectively. Recursive partitioning identified three genes each as significant determinants for recurrence and overall survival. Considering all the genes identified by either the univariate or partitioning analyses, four were found to significantly predict both recurrence and survival (JUN, MAP2K6, STAT3, and ICAM1); overexpression was associated with worse outcome. Comparing the favorable (low or normal) expression of $\geq$3/4 versus $\leq$2/4 of these oncogenes showed 5-year recurrence probabilities of 41% versus 88%, respectively (P<0.001), and 5-year overall survival probabilities of 61% versus 5%, respectively (P<0.001). The prognostic potential of this 4-gene panel was confirmed on a large independent external cohort (disease-specific survival P=0.039). Thus, as disclosed herein, the inventors document the generation of a concise, biologically relevant 4-gene panel that significantly predicts recurrence and survival, and that can also identify therapeutic targets for UC.

In one embodiment, the present invention provides a method of prognosing cancer characterized by disease recurrence despite possible future treatment with definitive surgery in an individual by determining the presence or absence of a high level of expression in the individual relative to a normal baseline standard of at least two risk markers selected from the group consisting of JUN, MAP2K6, STAT3, and ICAM1, and prognosing the cancer based upon the presence of a high level of expression of at least two of the risk markers. In another embodiment, the cancer is urothelial carcinoma.

In another embodiment, the present invention provides a method of treating cancer characterized by disease recurrence despite possible future treatment with definitive surgery by determining the presence of a high expression relative to a normal baseline standard of at least two risk markers selected from the group consisting of JUAN, MAP2K6, STAT3 and/or ICAM1 and treating the cancer. In another embodiment, the cancer is urothelial carcinoma. In another embodiment, the presence of a high expression of JUN, MAP2K6, STAT3 and/or ICAM1 relative to a normal baseline standard provide therapeutic targets for treating urothelial carcinoma.

In another embodiment, the present invention provides a prognostic panel containing any of the following markers: JUN, MAP2K6, STAT3, ICAM1, insulin-like growth factor 1 (IGF1), superoxide dismutase 1(SOD1), B-cell lymphoma 2 (BCL2), bone morphogenetic protein 6 (BMP6), mitogen-activated protein kinase 12 (MAPK12), tumor necrosis factor superfamily member 10 (TNFSF10), cyclin A2 (CCNA2), BCL2-like 1 (BCL2L1), transforming growth factor-beta-induced factor (TGIF), FOS-like antigen 1 (FOSL1) and glutathione S-transferase M3 (GSTM3). In another embodiment, the panel is a single prognostic panel consisting essentially of six, seven, eight, nine, ten or eleven of the markers. In another embodiment, four of the markers consist essentially of the following markers: JUN, MAP2K6, STAT3, ICAM1.

In another embodiment, the present invention provides a prognostic panel containing any of the following markers: JUN, MAP2K6, STAT3, ICAM1, insulin-like growth factor 1 (IGF1), superoxide dismutase 1 (SOD1), B-cell lymphoma 2 (BCL2), bone morphogenetic protein 6 (BMP6), mitogen-activated protein kinase 12 (MAPK12), tumor necrosis factor superfamily member 10 (TNFSF10), cyclin A2 (CCNA2), BCL2-like 1 (BCL2L1), transforming growth factor-beta-induced factor (TGIF), FOS-like antigen 1 (FOSL1) and glutathone S-transferase M3 (GSTM3). In another embodiment, the panel is a single prognostic panel consisting essentially of six, seven, eight, nine, ten or eleven of the markers. In another embodiment, four of the markers consist essentially of the following markers: JUN, MAP2K6, STAT3, ICAM1.

In another embodiment, the present invention provides an eight gene prognostic panel for recurrence and/or survival of urothelial carcinoma. In another embodiment, the eight gene prognostic panel consists essentially of the following markers: JUN, MAP2K6, STAT3, ICAM1, IGF1, SOD1, BCL2, and BMP6.

The present invention is also directed to a kit to diagnose, prognose and/or treat cancer, such as for practicing the inventive method of analyzing the expression of JUN, MAP2K6, STAT3 and/or ICAM1 for the prognosis and predicting the progression of bladder or urothelial cancer. Or, for example, the kit may contain a prognostic panel with any of the following markers: JUN, MAP2K6, STAT3, ICAM1, insulin-like growth factor 1 (IGF1), superoxide dismutase 1(SOD1), B-cell lymphoma 2 (BCL2), bone morphogenetic protein 6 (BMP6), mitogen-activated protein kinase 12 (MAPK12), tumor necrosis factor superfamily member 10 (TNFSF10), cyclin A2 (CCNA2), BCL2-like 1 (BCL2L1), transforming growth factor-beta-induced factor (TGIF), FOS-like antigen 1 (FOSL1) and glutathione S-transferase M3 (GSTM3).

The present invention is also directed to a kit to diagnose, prognose and/or treat cancer, such as for practicing the inventive method of analyzing the expression of JUN, MAP2K6, STAT3 and/or ICAM1 for the prognosis and predicting the progression of bladder or urothelial cancer. Or, for example, the kit may contain a prognostic panel with any of the following markers: JUN, MAP2K6, STAT3, ICAM1, insulin-like growth factor 1 (IGF1), superoxide dismutase 1 (SOD1), B-cell lymphoma 2 (BCL2), bone morphogenetic protein 6 (BMP6), mitogen-activated protein kinase 12 (MAPK12), tumor necrosis factor superfamily member 10 (TNFSF10), cyclin A2 (CCNA2), BCL2-like 1 (BCL2L1), transforming growth factor-beta-induced factor (TGIF), FOS-like antigen 1 (FOSL1) and glutathone S-transferase M3 (GSTM3). The kit is an assemblage of materials or components, including at least one of the inventive compositions. Thus, in some embodiments the kit contains a composition including markers for detecting and amplifying expression of JUN, MAP2K6, STAT3 ad/or ICAM1, as described above.

Instructions for use may be included in the kit. "Instructions for use" typically include a tangible expression describing the technique to be employed in using the components of the kit to effect a desired outcome, such as to prognose or predict progression of bladder cancer. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

A variety of methods can be used to determine the presence or absence of gene expression. As an example, enzymatic amplification of nucleic acid from an individual may be used to obtain nucleic acid for subsequent analysis. The presence or absence of gene expression may also be determined directly from the individual's nucleic acid without enzymatic amplification.

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

The presence or absence of gene expression may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

Other molecular methods useful for determining the presence or absence of gene expression are known in the art and useful in the methods of the invention. Other well-known approaches for determining the presence or absence of gene expression include automated sequencing and RNAase mismatch techniques (Winter et al., Proc. Natl. Acad. Sci. 82:7575-7579 (1985)). Furthermore, one skilled in the art understands that, where the presence or absence of expression of multiple genes is to be determined, individual gene expression can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that expression of multiple genes can be detected in individual reactions or in a single reaction (a "multiplex" assay). In view of the above, one skilled in the art realizes that the methods of the present invention for prognosing an individual may be practiced using one or any combination of the well known assays described above or another art-recognized genetic assay.

There are also many techniques readily available in the field for detecting the presence or absence of polypeptides or other biomarkers, including protein microarrays. For example, some of the detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Similarly, there are any number of techniques that may be employed to isolate and/or fractionate biomarkers. For example, a biomarker may be captured using biospecific capture reagents, such as antibodies, aptamers or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer and hybrids of these.

Alternatively, for example, the presence of biomarkers such as polypeptides maybe detected using traditional immunoassay techniques. Immunoassay requires biospecific capture reagents, such as antibodies, to capture the analytes. The assay may also be designed to specifically distinguish protein and modified forms of protein, which can be done by employing a sandwich assay in which one antibody captures more than one form and second, distinctly labeled antibodies, specifically bind, and provide distinct detection of, the various forms. Antibodies can be produced by immunizing animals with the biomolecules. Traditional immunoassays may also include sandwich immunoassays including ELISA or fluorescence-based immunoassays, as well as other enzyte immunoassays.

Prior to detection, biomarkers may also be fractionated to isolate them from other components in a solution or of blood that may interfere with detection. Fractionation may include platelet isolation from other blood components, sub-cellular fractionation of platelet components and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Patient Selection

The study cohort comprised 58 UC patients (mean age 69.5 years) and five normal controls. Frozen CC tissue was obtained after radical cystectomy from 49 patients at the University of Southern California and 9 patients at the University of California, San Francisco between 1991 and 2002. These included patients with invasive (T1-T4) tumors, and noninvasive (Ta) tumors refractory to bladder-conserving therapies. Specifically, the study cohort included 10 Ta, 11 T1, 10 T2, 21 T3 and 6 T4 patients. Patients with distant metastasis at the time of diagnosis were excluded. TNM staging was standardized to the 2002 AJCC recommendations[1]. Controls consisted of normal urothelium from the bladder neck of patients who underwent radical prostatectomy for localized prostatic adenocarcinoma without bladder involvement and no history of UC.

8 patients (13.8%) received adjuvant chemotherapy and/or radiotherapy. These included patients with high grade, recurrent noninvasive (n=1), muscle-invasive (n=2), extravesically extending (n=1), and nodal metastasized (n=4) tumors. Mean follow-up was 3.04 years (range, 0.30-10.44 years) during which 29 patients recurred and 38 patients died. UC was the cause of death in 30 patients, while 8 patients died due to undocumented causes. While the cohort had a modest follow-up duration, this was primarily due to early deaths rather than a loss to follow-up. The mean follow-up was longer in patients with no recurrences at the end of the study (3.69 years) than those who recurred (2.39 years). Similarly, patients alive at the end of the study also had a longer mean follow-up (4.5 years) than those who died (2.28 years). All patients in the cohort who received adjuvant therapy eventually recurred and died. While adjuvant therapy did delay the mean time of first recurrence (mean=1.5 years) compared to patients who did not receive any therapy besides surgery (mean=1.07 years), all patients receiving adjuvant therapy were followed up until death, thereby avoiding drawbacks of short follow-up in these cases. Informed consent was obtained from all patients. The study was approved by the respective Institutional Review Boards.

Example 2

StaRT-PCR, and Comparison of Tumor and Normal Gene Expression Levels

After RNA extraction by the conventional TRIzol method (Invitrogen, Carlsbad, Calif.), cDNA was prepared and quantitative gene expression profiling performed by StaRT-PCR (Gene Express, Toledo, Ohio), as previously described[7,8]. The internal standard mixtures (A-F, over six logs of concentration) contained competitive templates (CT) of 69 transcripts in addition to 600,000 β-actin CT molecules/μL (Gene Express, Toledo, Ohio). For each sample, StaRT-PCR analysis was performed using five different CT mixes (B-F). Thus each sample underwent five separate PCR analyses; each separate reaction containing the ready-to-use master mixture, cDNA sufficient for expression measurements of the 70 transcripts (including β-actin), primers for the 70 transcripts and one of the five CT mixes (B-F). Following PCR, the amplification products were electrophoresed, and image analysis and quantitation of band fluorescence intensities were done as described previously[7]. The expression of each gene was reported as number of mRNA molecules per $10^6$ molecules of β-actin.

Following log transformation, each transcript expression level for all UC cases was compared to the respective mean level in normal urothelium. Any tumor transcript level >2 standard deviations over the mean expression level in normal urothelium was labeled as overexpressed, while any expression level <2 standard deviations under the mean level in normal urothelium was labeled as underexpressed. Tumor transcript expression levels between two standard deviations above or below the mean levels in normal urothelium were labeled as normally expressed. Thus, all tumor transcripts were assigned expression "values" (low/normal/high) depending on their levels compared to normal urothelium. Once the significant genes were identified, each transcript expression was dichotomized into "favorable" and "unfavorable" depending on the outcome associated with respective expression values.

Example 3

Data Analysis

The clinical outcomes analyzed were time to recurrence, disease-specific survival, and overall survival. Time to recurrence was calculated from date of cystectomy to the first date of clinical recurrence or progression. Patients without recurrence or progression were censored at the time of death or last follow-up. Disease-specific survival was calculated from date of cystectomy to the date of death from UC or the last follow-up date. Overall survival was calculated from date of cystectomy to the date of death from any cause; patients who were still alive were censored at the date of last follow-up. Time to recurrence was preferred over disease-specific survival since currently most patients who die of UC have a documentation of disease recurrence; overall survival also accounts for cases where cause of death may be unknown and where the impact of UC treatment may contribute to death although the disease does not recur.

The log-rank test[9] was used to examine associations between clinical parameters and gene expression values, and clinical outcome. In univariate analysis, the relative risk ratio and its associated 95% confidence interval were based on the log-rank test[10]. To adjust for multiple comparisons and control the false-positive rate, bootstrap internal validation was done for all genes identified by univariate analysis, thereby eliminating the possibility of overfitting or biasing conclusions on a small subset[11]. 1000 bootstrap samples of 58 observations each were drawn from the original UC cohort using simple random sampling with replacement. Selected genes were retained if associated $P \leq 0.050$ in >500 simulations[12,13]. Reported P values are two-sided.

Three multivariable approaches were adopted. The first approach used nonparametric classification and regression trees based on recursive partitioning (RP) to explore the gene expression variables and separate patients into prognostic subgroups based on time to recurrence and overall survival[14,15]. In this case, a nonparametric classification and regression tree method based on RP was used to explore the gene expression variables and categorize patients into prognostic subgroups based on time to recurrence and overall survival[14,15]. This included two processes: "tree growing" and "tree pruning"[14]. Tree growing started with all patients in one group and made a series of binary recursive splits based on an expression value cutoff that yielded subgroups with the greatest dissimilarity in clinical outcome. Tree pruning was then performed to produce simpler subtrees by assessing the misclassification error associated with a particular subtree. RP analysis was performed using the RPART unction in the S-Plus library (insightful, Seattle, Wash.)[15]. The second approach used stepwise, forward selection based on the Cox proportional hazards model, stratified by pathologic stage and by lymph node density. Thirdly, Akaike information criterion (AIC) within a Cox proportional hazards model, stratified by pathologic stage, was used to demonstrate the discriminatory ability of the gene panels[16]. A smaller AIC value indicates a more desirable panel for predicting outcome[17].

Functional analysis of pathways affected by the differentially expressed genes was also conducted using MetaCore (GeneGo, St. Joseph, Mich.). Dijkstra's shortest paths algorithm was employed to connect the significant genes by the shortest curated network paths[18]. The number of steps in the path was restricted to a maximum of two to visualize the nearest directly interacting molecules and most significantly affected pathways.

Example 4

External Validation

For validation purposes, multiple public repositories were searched for expression profiling data from independent external UC cohorts that encompassed all stages and provided publicly available corresponding clinical outcome information. The study by Sanchez-Carbayo et al[19] provided such a dataset online that also profiled all genes investigated in the present cohort. The study used 157 tissue samples from 105 UC patients (Ta-T4), and included whole genome profiles of primary tumors and "adjacent normal" urothelium generated using U133A human GeneChips (Affymetrix, Inc., Santa Clara, Calif.). Standard demographic and clinicopathologic information on the patients devoid of identifiers, and their corresponding clinical outcome information were publicly available. The inventors used the same binary outcome as defined in that study; whether the patient was dead of UC or had no evidence of disease at last follow-up. As true normal urothelium was not used in this study, and "adjacent normal" urothelium can potentially harbor genetic alterations similar to the adjacent tumor tissue[20], the expression profiles of the "adjacent normal" urothelium were disregarded for the current analysis. The final validation cohort consisted of expression profiles from primary tumors of 91 UC patients (mean age 67.8 years). Specifically, the final validation cohort included gene expression data from 2 Ta, 23 T1, 10 T2, 45 T3 and 11 T4 patients, several of them available in duplicates.

After log transformation, representative probe sets for the 11 genes predictive for overall survival from the inventors' analysis were chosen for validation in the external dataset[21], as survival was the only clinical outcome available for this cohort. In choosing representative probe sets, non-cross reacting accurate-type (at) probe sets were preferred over cross reacting-types (x_at, s_at), and a cluster that was supported by a DNA or full-length mRNA were preferred[21]. The probe sets chosen were 206106_at (MAPK12), 213281_at (JUN), 202688_at (TNFSF10), 208991_at (STAT3), 203418_at (CCNA2), 202637_s_at (ICAM1), 215037_s_at (BCL2L1), 205699_at (MAP2K6), 203313_s_at (TGIF), 204420_at (FOSL1), 202554_s_at (GSTM3). Expression of any gene below and above its median expression level in the validation cohort was considered favorable and unfavorable, respectively, in accordance with the findings from the study cohort. In case of duplicate samples, when any gene was overexpressed in any tumor duplicate, the gene was considered overexpressed in the tumor. The expression data was analyzed by the Partek Genomics Suite (Partek Inc., St. Louis, Mo.). Pearson's chi-square test was used to examine associations with clinical outcome.

Example 5

Clinicopathologic Parameters and Clinical Outcome

Associations of clinicopathologic parameters of the study cohort with outcome are listed in FIG. 3 herein. Pathologic stage was significantly associated with overall survival but not time to recurrence. Interestingly, 3/10 Ta,N-patients had post-cystectomy pelvic recurrences, demonstrating an unusually aggressive clinical course. In contrast, 9/11 T3/4,N-patients showed an unusually indolent clinical course with no recurrence at last follow-up.

Example 6

Individual Genes and Clinical Outcome

By univariate analysis, STAT3 (P=0.009), IGF1 (P=0.021), JUAN (P=0.026), SOD1 (P=0.033), and MAP2K6 (P=0.044) were significantly associated with time to recurrence [FIG. 4 herein]. BCL2 (P=0.055) also showed a trend towards significance for time to recurrence. The consistency of these findings was supported by bootstrap analysis that selected the above transcripts in over half of the bootstrap samples for recurrence.

MAPK12 (P<0.001), JUN (P=0.001), TNFSF10 (P=0.007), CCNA2 (P=0.009), ICAM1 (P=0.014), BCL2L1 (P=0.015), MAP2K6 (P=0.016), TGIF (P=0.047), and STAT3 (P=0.050) were significantly associated with overall survival [FIG. 4 herein]. FOSL1 (P-0.051) also showed a trend towards significance for overall survival. Bootstrap analysis confirmed the consistency of these findings by selecting the above genes in over half of the bootstrap samples for overall survival.

Example 7

Inter-Dependent Gene Expressions and Clinical Outcome

RP analysis was performed to identify any gene that may, by itself, not be prognostically important and thus not feature in the univariate analysis, but in association with other genes, may be associated with clinical outcome. The expressions of BMP6, SOD1 and ICAM1 were identified as joint determinants for recurrence [FIG. 1A herein]. 87% patients with low BMP6 and high SOD1 (group 1a) remained recurrence-free at the end of the study, while this was seen in only 14% patients with normal or high BMP6 and high ICAM1 (group 1d); low BMP6 with low or normal SOD1 (group 1b), and normal or high BMP6 with low or normal ICAM1 (group 1c) showed intermediate recurrence probabilities. Log-rank analysis of these four groups showed significant association with time to recurrence (P<0.001), with group 1a demonstrating the lowest and group 1d demonstrating the highest probability of recurring [FIG. 1B herein].

MAPK12, GSTM3 and ICAM1 were identified as joint determinants for overall survival [FIG. 1C herein]. 89% patients with low MAPK12 and GSTM3 (group 2a) survived at the end of the study, in contrast to 0% patients with normal or high MAPK12 and high ICAM (group 2d). Patients with low MAPK12, and normal or high GSTM3 (group 2b) and normal or high MAPK12 with low or normal ICAM1 (group 2c) had intermediate survival probabilities. Log-rank analysis of these four groups also showed significant association with overall survival (P<0.001) with group 2a having the best and group 2d having the worst survival probabilities [FIG. 1D herein].

Example 8

Combined Analysis of Four Common Genes

The inventors believed that the most biologically relevant genes would predict both recurrence and overall survival by univariate and/or RP analyses. JUN, MAP2K6, and STAT3 were significantly associated with time to recurrence and overall survival by univariate analysis, and ICAM1 was significantly associated with overall survival by univariate analysis, and with recurrence and overall survival by RP analysis.

Figure 2:
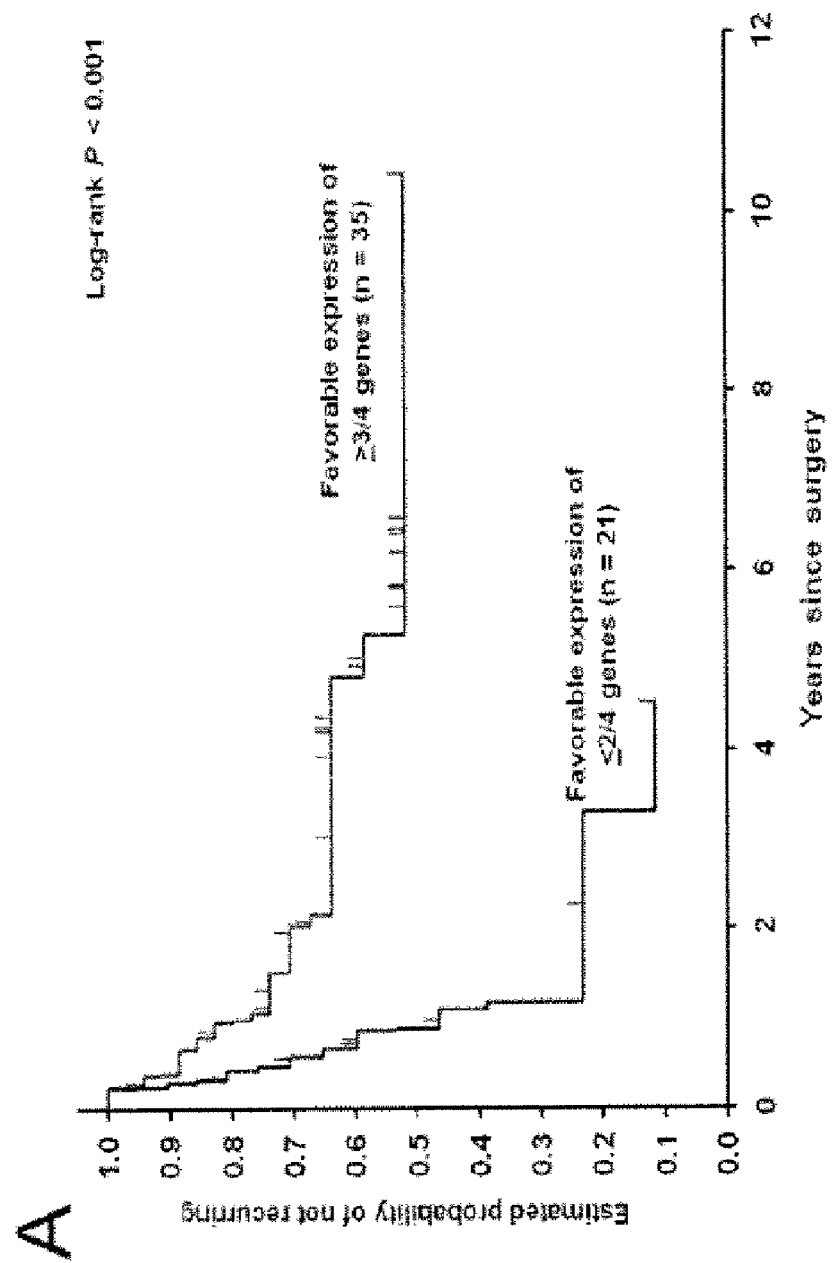
FIG. 2 depicts, in accordance with an embodiment herein, the generation of a predictive expression signature in urothelial carcinoma. Groups generated based on low or normal (favorable) expression of $\geq 3/4$ or $\leq 2/4$ genes among JUN, MAP2K6, STAT3, and ICAM1 showed significant differences in probabilities of (A) recurrence, (B) disease-specific survival, and (C) overall survival. (D) The performance of this 4-gene panel compared favorably to the 8-gene (SATS3, IGF1, JUN, SOD1, MAP2K6, BCL2, BMP6, and ICAM1) and 11-gene (MAPK12, JUN, TNFSF10, CCNA2, ICAM1, BCL2 L1, MAP2K6, TGIF, STAT3, FOSL1, and GSTM3) panels for prediction of time to recurrence and overall survival, respectively. AIC, Akaike information criterion.
Figure 2:
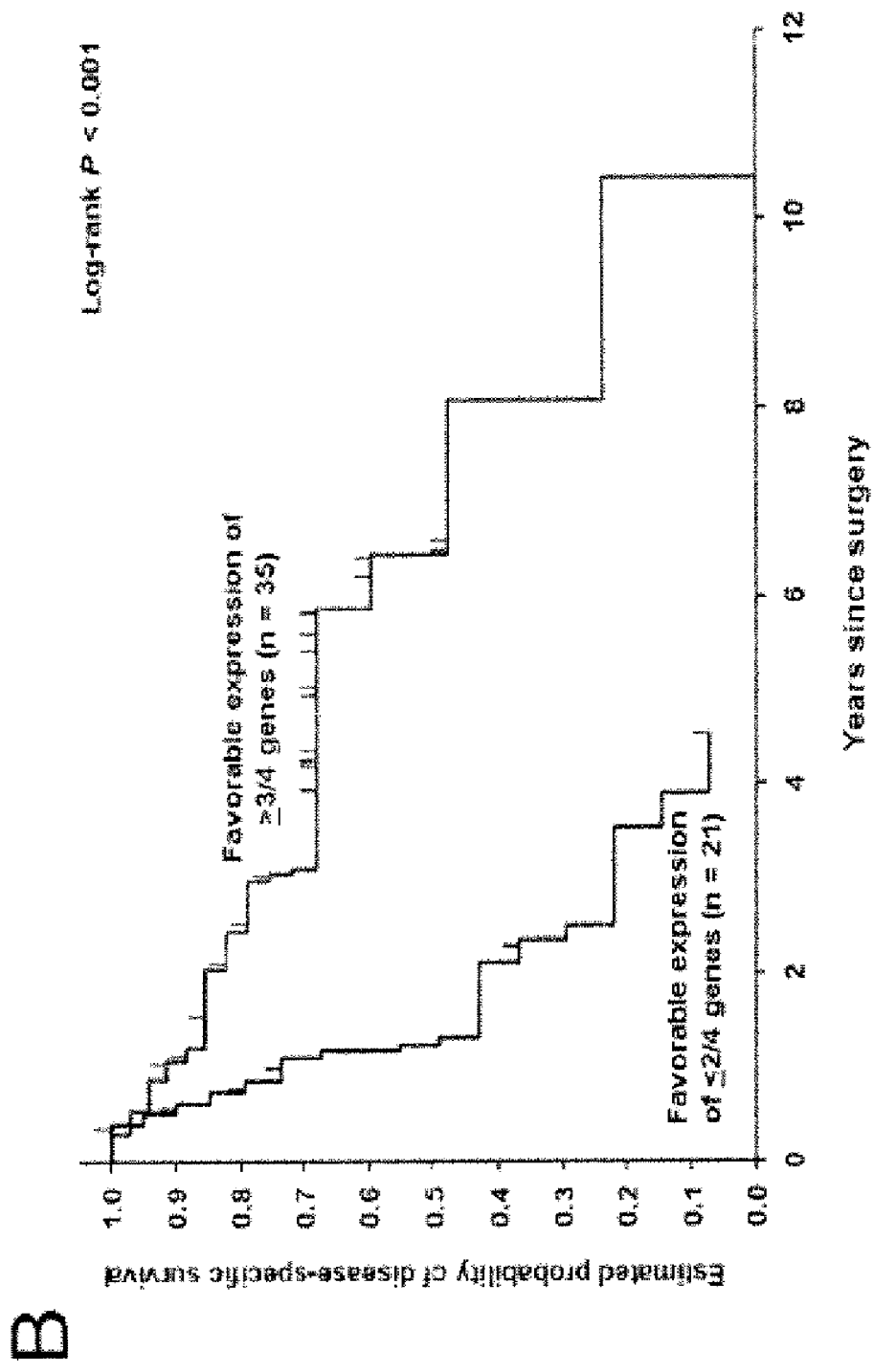
Figure 2:
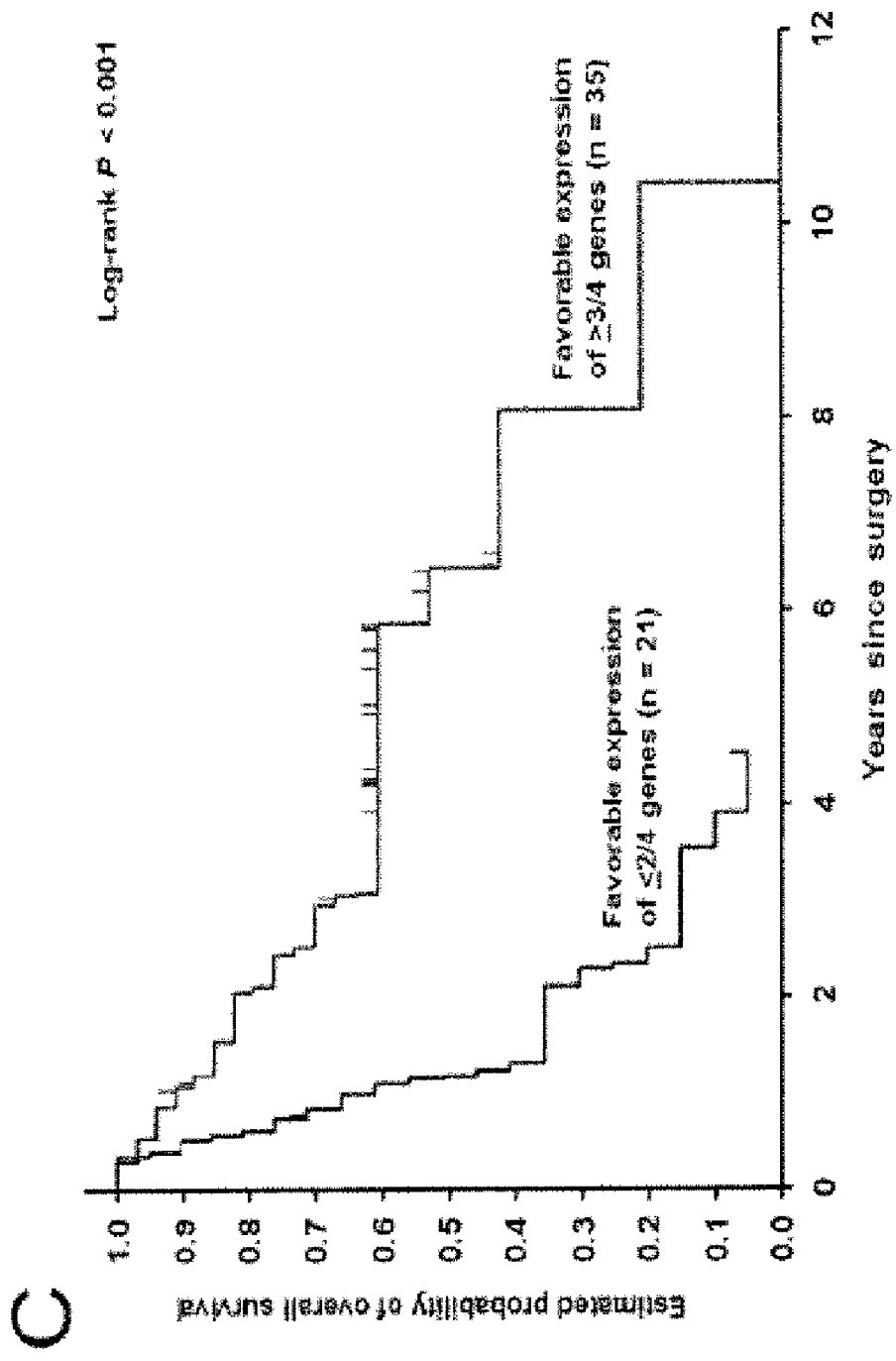
Figure 2:
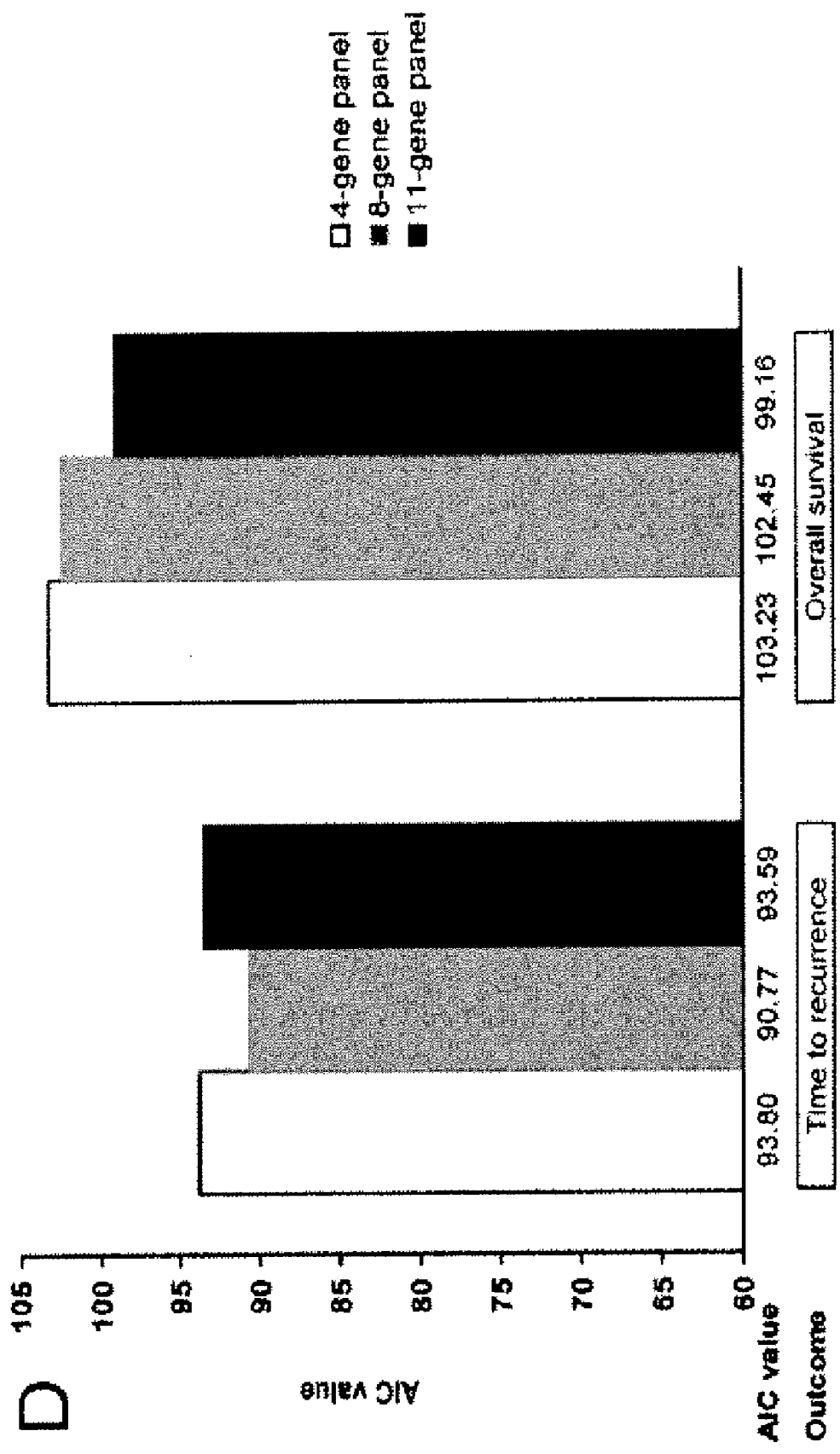
Figure 8B:
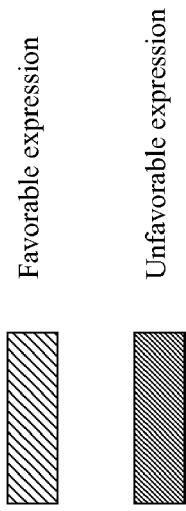
FIG. 8 depicts, in accordance with an embodiment herein, classification of subjects into favorable and unfavorable expressions of individually prognostic genes based on their expression patterns.

Based on the comparison of individual gene expression patterns with outcome, low or normal expression was found to be favorable, while overexpression was unfavorable. This was consistent with their functions as oncogenes[8,22,23]. The study cohort was then divided into two groups: patients with favorable (low or normal) expression of ≧3/4 genes (n=35), and patients with favorable expression of ≦2/4 genes (n=21). Two patients were excluded from the analysis as they had two favorable, one unfavorable, and one missing gene expression and could thus not be confidently classified into either group. The 5-year recurrence probabilities in these groups were 41% and 88%, respectively (P<0.001; FIG. 2A herein), the 5-year disease-specific survival probabilities were 68% and 7%, respectively (P<0.001; FIG. 2B herein), and the 5-year overall survival probabilities were 61% and 5%, respectively (P<0.001; FIG. 2C and FIG. 5 herein). To confirm that these differences were not due to inherent differences in the pathologic stages, the analysis was repeated, stratifying by each stage, and the results and patterns remained consistent. In a sensitivity analysis, the gene panel was re-evaluated employing the Cox proportional hazards model, stratified by pathologic stage and by lymph lode density. When patients with favorable expression of ≧3/4 genes were used as the reference croup, the relative risk of recurrence for patients with favorable expression of ≦2/4 genes was 3.09 and 2.63, respectively, and the relative risk of dying was 4.48 and 4.11, respectively. These relative risks remained statistically significant even after excluding the eight patients who received adjuvant treatment, indicating that the predictive value of these four genes was not altered by adjuvant therapy.

Interestingly, all three Ta,N-patients with pelvic recurrences had expression profiles consistent with a high recurrence risk (favorable expression of ≦2/4 genes). Similarly, 6/7 Ta,N- and 7/9 T3/4,N-patients without recurrences had expression profiles consistent with a low recurrence risk (favorable expression of ≧3/4 genes).

Example 9

Relative Predictive Power of Gene Panels

To assess how much predictive power was lost upon exclusion of the significant genes that were not common predictors of recurrence and overall survival, AIC within a Cox proportional hazards model, stratified by pathologic stage, was used to compare the 4-gene panel (consisting of JUN, MAP2K6, STAT3, and ICAM1), with the 8-gene and 11-gene panels (that contained genes individually predictive for recurrence and overall survival, respectively, by univariate and/or RP analyses). Expressions of these genes were dichotomized into favorable and unfavorable based on their association with outcome, and patients missing expression values for these genes were excluded for this analysis. While the 8-gene (STAT3, IGF1, JUN, SOD1, MAP2K6, BCL2, BAMP6, and ICAM1) and 11-gene (MAPK12, JUN, TNFSF10, CCNA2, ICAM1, BCL2L1, MAP2K6, TGIF, STAT3, FOSL1, and GSTM3) panels expectedly performed the best in predicting time to recurrence and overall survival, respectively, their performance was not substantially superior to the 4-gene panel [FIG. 2D herein]. In fact, the differences in the AIC values between the 4-gene panel and the best performing panels for time to recurrence and overall survival were 3.03 and 4.07, respectively. This suggested that the predictive performances of these panels were empirically comparable as the absolute differences in the AIC values were close to or less than 4[17].

Example 10

Validation of Identified Gene Panels

An independent external UC cohort[19], profiled for their gene expressions using oligonucleotide microarrays, was used to confirm the prognostic potential of the identified gene panels. As the cohort only reported disease-specific survival, the 11-gene predictive panel for overall survival and the common 4-gene panel were chosen for validation. Associations of clinicopathologic parameters with disease-specific survival are listed in FIG. 6 herein. The cohort was divided into two groups based on the 11-gene panel: patients with favorable expression of ≧7/11 genes (n=56), and patients with favorable expression of ≦6/11 genes (n=35). Using the former as the reference group, the relative risk of disease-specific death in patients with favorable expression of ≦6/11 genes was 2.00 (P=0.007). To assess the predictive power of the common 4-gene panel, the validation cohort was again divided into two groups: patients with favorable expression of ≧3/4 genes (n=50), and patients with favorable expression of ≦2/4 genes (n=41). Using the former as the reference group, the relative risk of disease-specific death in patients with favorable expression of ≦2/4 genes was 1.71 (P#0.039).

Example 11

Generally

The inventors used a quantitative, pathway-specific approach to profile genes that feature in important cellular pathways that are crucial in UC development. The choice for the final predictive panel was based on the belief that the most biologically relevant genes should be able to predict both recurrence and survival. In this study, the 4-gene panel (JUN, MAP2K6, STAT3, and ICAM1) is a highly significant predictor of these outcomes, independent of standard prognostic criteria (stage, grade and lymph node density). Further, this panel identifies high-risk patients, with nearly all patients recurring and dying if ≦2/4 genes have favorable expression. The prognostic potential of this panel was further supported by an external dataset that profiled genes using a completely different methodology, thereby demonstrating the robustness of this 4-gene panel in predicting clinical outcome.

Gene expression profiles are usually generated using microarrays. These studies can suffer from inconsistencies in results and lack of reproducibility across platforms[24,25]. Furthermore, the output often contains >20-100 genes, which can dilute biologic and clinical relevance while increasing noise and opportunities for random chance. Thus, there was an identification of key genes and associated pathways of prognostic value.

The univariate analysis identified six and ten genes that were associated with recurrence and overall survival, respectively. The protein products of IGF1, JUN, MAP2K6, BCL2, CCNA2, ICAM1, BCL2L1, TGIF, and FOSL1 have been associated with poor prognosis in several cancers including bladder[8,22,26-31]. High expression of these genes was associated with worse prognosis, consistent with their biologic roles as oncogenes. As described herein, the inventors demonstrate that constitutive activation of the MAPK pathway in UC[5]; low MAPK12 was associated with higher probability of overall survival. STAT3 overexpression corresponded to poorer prognosis, consistent with observations that STAT3 increases UC cell lines' invasiveness[23]. Low SOD1 corresponded with decreased recurrence probability, consistent with findings in acute myelogenous leukemia and lymphoproliferative syndromes[32]. Although TRAIL, the protein product of TNFSF10, induces apoptosis, patients with increased TNFSF10 showed poorer overall survival. This patient subset was insensitive to TRAIL-mediated apoptosis, consistent with findings that different UC cell lines have varying degrees of susceptibility to TRAIL[33].

The RP analysis also selected DMP6 and ICAM1 as joint determinants of recurrence. BMP6 promotes tumor angiogenesis, and elevated ICAM1 is associated with increased UC metastatic potential[8,34]. Patients with low BMP6 and high SOD1 had the lowest recurrence rates, while those with normal or high DMP6 and high ICAM1 expression had the highest. GSTM3 was also associated with overall survival by RP analysis. GSMT3 polymorphisms are linked to carcinogenesis, and GSTM3 mutations are associated with increasing UC risk[35]. In patients with low MAPK12, those with low GSTM3 showed the highest survival probability, while those with normal or high GSTM3 had the lowest.

When the interrelationships between proteins transcribed from these genes were examined by functional analysis[18], nine direct and >150 indirect interactions were discovered, thereby highlighting the importance of their crosstalk. This led to focus on genes that could predict both recurrence and survival. Obtaining a concise prognostic marker list is crucial in such studies as clinical applications of such panels are more cost-effective and practical. Previous prognostic panels have usually featured markers from a single cellular pathway[36,37]. The 4-gene panel obtained after profiling genes across multiple pathways robustly predicted clinical outcome. Additionally, the ability of this panel to accurately predict recurrence independent of stage can be a useful supplement to routine staging. Furthermore, MAP2K6 and ICAM1 were also previously identified to predict nodal metastasis in UC[8]. Validation of the 4- and 11-gene panels on the external dataset was consistent with AIC observations that while the 11-gene panel could expectedly predict survival, its performance was not substantially superior to the 4-gene panel. Moreover, the validation highlighted the robustness of the 4-gene panel, independent of the platform used for profiling the genes.

In conclusion, using a multiplexed, biologically-driven approach, the inventors have identified a panel comprising of JUN, MAP2K6, STAT3, and ICAM1 that can predict clinical outcome in UC independent of conventional prognostic criteria, and can identify patients with operable UC that will recur despite definitive surgery alone. These patients would clearly benefit from additional therapy. Increasing numbers of alterations in these genes predict poorer prognosis. These genes and their associated pathways can serve as outcome predictors and therapeutic targets in UC.

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

1. Urinary bladder, in Greene F L, Page D L, Fleming I D, et al (eds): AJCC Cancer Staging Manual (ed 6). New York, Springer-Verlag, 2002, pp 367-74

2. Mitra A P, Datar R H, Cote R J: Molecular staging of bladder cancer. BJU Int 96:7-12, 2005
3. Brambilla C, Fievet F, Jeanmart M, et al: Early detection of lung cancer: role of biomarkers. Eur Respir J Suppl 39:36s-44s, 2003
4. Northup J K, Gadre S A, Ge Y, et al. Do cytogenetic abnormalities precede morphologic abnormalities in a developing malignant condition? Eur J Haematol 78:152-6, 2007
5. Mitra A P, Datar R H, Cote R J: Molecular pathways in invasive bladder cancer: New insights into mechanisms, progression, and target identification. J Clin Oncol 24:5552-64, 2006
6. Willey J C, Crawford E L, Jackson C M, et al: Expression measurement of many genes simultaneously by quantitative RT-PCR using standardized mixtures of competitive templates. Am J Respir Cell Mol Biol 19:6-17, 1998
7. Pagliarulo V, George B, Beil S J, et al: Sensitivity and reproducibility of standardized-competitive RT-PCR for transcript quantification and its comparison with real time RT-PCR. Mol Cancer 3:5, 2004
8. Mitra A P, Almal A A, George B, et al: The use of genetic programming in the analysis of quantitative gene expression profiles for identification of nodal status in bladder cancer. BMC Cancer 6:159, 2006
9. Miller R G: Survival analysis. Wiley series in probability and mathematical statistics. New York, N.Y., John Wiley, 1981, pp 44-102
10. Berry G, Kitchin R M, Mock P A: A comparison of two simple hazard ratio estimators based on the logrank test. Stat Med 10:749-55, 1991
11. Harrell F E, Jr., Lee K L, Mark P B: Multivariable prognostic models: Issues in developing models, evaluating assumptions and adequacy, and measuring and reducing errors. Stat Med 15:361-87, 1996
12. Chen C H, George S L: The bootstrap and identification of prognostic factors via Cox's proportional hazards regression model. Stat Med 4:39-46, 1985
13. Altman D G, Andersen P K: Bootstrap investigation of the stability of a Cox regression model. Stat Med 8:771-83, 1989
14. Breiman L, Friedman J H, Olshen A, et al: Classification and regression trees, Belmont, Calif., Wadsworth International Group, 1984
15. Therneau T M, Atkinson E J: An introduction to recursive partitioning using the RPART routines, Mayo Clinic Biostatistics Technical Report. Rochester, Minn., Mayo Foundation, 1997
16. Akaike H: A new look at the statistical model identification. IEEE Trans Automat Contr AC-19:716-23, 1974
17. Formal inference from more than one model: Multimodel inference (MMI), in Burnham K P, Anderson D R: Model Selection and Multimodel Inference. A Practical Information-Theoretic Approach (ed 2). New York, N.Y., Springer-Verlag, 2002, pp 149-205
18. Dijkstra E W: A note on two problems in connexion with graphs. Numer Math 1:269-71, 1959
19. Sanchez-Carbayo M, Socci N D, Lozano J, et al: Defining molecular profiles of poor outcome in patients with invasive bladder cancer using oligonucleotide microarrays. J Clin Oncol 24:778-89, 2006
20. Braakhuis B J, Tabor M P, Kummer J A, et al: A genetic explanation of Slaughters concept of field cancerization: Evidence and clinical implications. Cancer Res 63:1727-30, 2003
21. Affymetrix: Array design for the GeneChip Human Genome U 133 Set (Part Number 701133 Rev. 2). Santa Clara, Calif., 2007, pp 12
22. Tiniakos D G, Mellon K, Anderson J J, et al: c-jun oncogene expression in transitional cell carcinoma of the urinary bladder. Br J Urol 74:757-61, 1994
23. Itoh M, Murata T, Suzuki T, et al: Requirement of STAT3 activation for maximal collagenase-1 (MMP-1) induction by epidermal growth factor and malignant characteristics in T24 bladder cancer cells. Oncogene 25:1195-204, 2006
24. Schultz I J, Wester K, Straatman X, et al: Prediction of recurrence in Ta urothelial cell carcinoma by real-time quantitative PCR analysis: A microarray validation study. Int J Cancer 119:1915-9, 2006
25. Kuo W P, Jenssen T K, Butte A J, et al: Analysis of matched mRNA measurements from two different microarray technologies. Bioinformatics 18:405-12, 2002
26. Zhao H, Grossman H B, Spitz M R, et al: Plasma levels of insulin-like growth factor-1 and binding protein-3, and their association with bladder cancer risk. J Urol 169:714-7, 2003
27. Hussain S A, Ganesan R, Hiller L, et al: BCL2 expression predicts survival in patients receiving synchronous chemoradiotherapy in advanced transitional cell carcinoma of the bladder. Oncol Rep 10:571-6, 2003
28. Blaveri E, Simko J P, Korkola J E, et al: Bladder cancer outcome and subtype classification by gene expression. Clin Cancer Res 11:4044-55, 2005
29. Korkolopoulou P, Lazaris A, Konstantinidou A E, et al: Differential expression of bcl-2 family proteins in bladder carcinomas. Relationship with apoptotic rate and survival. Eur Urol 41:274-83, 2002
30. Nakakuki K, Imoto I, Pimkhaokham A, et al: Novel targets for the 18p11.3 amplification frequently observed in esophageal squamous cell carcinomas. Carcinogenesis 23:19-24, 2002
31. Kraemer K, Schmidt U, Fuessel S, et al: Microarray analyses in bladder cancer cells: Inhibition of hTERT expression down-regulates EGFR. Int J Cancer 119:1276-84, 2006
32. Gonzales R, Auclair C, Voisin F, et al: Superoxide dismutase, catalase, and glutathione peroxidase in red blood cells from patients with malignant diseases. Cancer Res 44:4137-9, 1984
33. Steele L P, Georgopoulos N T, Southgate J, et al: Differential susceptibility to TRAIL of normal versus malignant human urothelial cells. Cell Death Differ 13:1564-76, 2006
34. Ren R, Charles P C, Zhang C, et al: Gene expression profiles identify a role for cyclooxygenase 2-dependent prostanoid generation in BMP6-induced angiogenic responses. Blood 109:2847-53, 2007
35. Schnakenberg E, Breuer R, Werdin R, et al. Susceptibility genes: GSTM1 and GSTM3 as genetic risk factors in bladder cancer. Cytogenet Cell Genet 91:234-8, 2000
36. Chatterjee S J, Datar R, Youssefzadeh D, et al: Combined effects of p53, p21, and pRb expression in the progression of bladder transitional cell carcinoma. J Clin Oncol 22:1007-13, 2004
37. Shariat S F, Tokunaga H, Zhou J, et al p53, p21, pRB, and p16 expression predict clinical outcome in cystectomy with bladder cancer. J Clin Oncol 22:1014-24, 2004

The invention claimed is:
1. A kit for prognostic use, comprising:
a single prognostic panel consisting essentially of: v-jun sarcoma virus 17 oncogene homolog (JUN), mitogen-activated protein kinase kinase 6 (MAP2K6), signal transducer and activator of transcription 3 (STAT3), and intercellular adhesion molecule 1 (ICAM1).

2. The kit of claim 1, further comprising reference markers, detection and amplification reagents for detecting the presence of markers and/or instructions for using the single prognostic panel.

3. A method of determining a prognosis of cancer characterized by disease recurrence despite possible future treatment with definitive surgery in an individual, comprising:
  determining the presence or absence of a high level of expression in the individual relative to a normal baseline standard for a single prognostic panel consisting essentially of the following markers: JUN, MAP2K6, STAT3, and ICAM1; and
  prognosing a case of cancer characterized by disease recurrence despite possible future treatment with definitive surgery if the individual demonstrates the presence of a high level of expression relative to a normal baseline standard of at least two of the markers.

4. The method of claim 3, wherein the presence of four of said markers presents a greater likelihood of a prognosis of cancer characterized by disease recurrence despite possible future treatment with definitive surgery than the presence of three or two of said markers, and the presence of three of said markers presents a greater likelihood of a prognosis of cancer characterized by disease recurrence despite possible future treatment with definitive surgery than the presence of two of said markers but less than the presence of four of said markers, and the presence of two of said markers presents a greater likelihood of a prognosis of cancer characterized by disease recurrence despite possible future treatment with definitive surgery than the presence of one or none of said markers but less than the presence of three or four of said markers.

5. The method of claim 3, wherein the cancer is urothelial carcinoma.

6. The method of claim 3, wherein the cancer is brain cancer, thyroid cancer, breast cancer, lung cancer, ovarian cancer, pituitary cancer and/or colon cancer.

7. A method of treating cancer characterized by disease recurrence despite possible future treatment with definitive surgery in an individual, comprising:
  determining the presence or absence of a high level of expression in the individual relative to a normal baseline standard for a single prognostic panel consisting essentially of the following markers: JUN, MAP2K6, STAT3, and ICAM1;
  prognosing a case of cancer characterized by disease recurrence despite possible future treatment with definitive surgery if the individual demonstrates the presence of a high level of expression relative to a normal baseline standard of at least two of the markers; and
  treating the cancer with a non-surgical treatment if the individual has a prognosis of a case of cancer characterized by disease recurrence despite possible future treatment with definitive surgery.

8. The method of claim 7, wherein the non-surgical treatment comprises chemotherapy.

9. A kit for prognostic use, comprising:
  a single prognostic panel consisting essentially of: JUN, MAP2K6, STAT3, ICAM1, insulin-like growth factor 1 (IGF1), superoxide dismutase 1(SOD1), B-cell lymphoma 2 (BCL2), bone morphogenetic protein 6 (BMP6), mitogen-activated protein kinase 12 (MAPK12), tumor necrosis factor superfamily member 10 (TNFSF10), cyclin A2 (CCNA2), BCL2-like 1 (BCL2L1), transforming growth factor-beta-induced factor (TGIF), FOS-like antigen 1 (FOSL1) and glutathione S-transferase M3 (GSTM3).

10. A method of determining a prognosis of cancer characterized by disease recurrence despite possible future treatment with definitive surgery in an individual, comprising:
  determining the presence or absence of a high level of expression in the individual relative to a normal baseline standard for a single prognostic panel consisting essentially of the following markers: JUN, MAP2K6, STAT3, ICAM1, IGF1, SOD1, BCL2, BMP6, MAPK12, TNFSF10, CCNA2, BCL2L1, TGIF, FOSL1 and GSTM3; and
  prognosing a case of cancer characterized by disease recurrence despite possible future treatment with definitive surgery if the individual demonstrates the presence of a high level of expression relative to a normal baseline standard of one or more of the markers.

11. A kit for prognostic use, comprising:
  a single prognostic panel consisting essentially of: JUN, MAP2K6, STAT3, ICAM1, IGF1, SOD1, BCL2, and BMP6.

12. A method of determining a prognosis of cancer characterized by disease recurrence despite possible future treatment with definitive surgery in an individual, comprising:
  determining the presence or absence of a high level of expression in the individual relative to a normal baseline standard for a single prognostic panel consisting essentially of: JUN, MAP2K6, STAT3, ICAM1, IGF1, SOD1, BCL2, and BMP6; and
  prognosing a case of cancer characterized by disease recurrence despite possible future treatment with definitive surgery if the individual demonstrates the presence of a high level of expression relative to a normal baseline standard of one or more of the markers.

13. A kit for prognostic use, comprising:
  a single prognostic panel consisting essentially of: MAPK12, JUN, TNFSF10, CCNA2, TGIF, MAP2K6, BCL2L1, STAT3, ICAM1, FOSL1, and GSTM3.

14. A method of determining a prognosis of cancer characterized by disease recurrence despite possible future treatment with definitive surgery in an individual, comprising:
  determining the presence or absence of a high level of expression in the individual relative to a normal baseline standard for a single prognostic panel consisting essentially of: MAPK12, JUN, TNFSF10, CCNA2, TGIF, MAP2K6, BCL2L1, STAT3, ICAM1, FOSL1, and GSTM3; and
  prognosing a case of cancer characterized by disease recurrence despite possible future treatment with definitive surgery if the individual demonstrates the presence of a high level of expression relative to a normal baseline standard of one or more of the markers.

* * * * *

UNITED STATES PATENT AND TRADEMARK OFFICE
CERTIFICATE OF CORRECTION

PATENT NO. : 8,293,880 B2
APPLICATION NO. : 12/411199
DATED : October 23, 2012
INVENTOR(S) : Richard J. Cote et al.

Page 1 of 1

It is certified that error appears in the above-identified patent and that said Letters Patent is hereby corrected as shown below:

In the Specification

In Column 1, Lines 9-14, cancel the text:
"GOVERNMENT RIGHTS
This invention was made with U.S. Government support on behalf of the National Institutes of Health grant CA-86871 and National Cancer Institute grant CA-14089. The U.S. Government may have certain rights in this invention."

And insert the following:
--STATEMENT REGARDING FEDERALLY SPONSORED RESEARCH OR DEVELOPMENT
This invention was made with government support under CA071921 and CA086871 awarded by the National Institutes of Health (NIH). The government has certain rights in the invention.--

Signed and Sealed this
First Day of December, 2020

Andrei Iancu
*Director of the United States Patent and Trademark Office*